US012782348B2

(12) United States Patent
Köhler et al.

(10) Patent No.: US 12,782,348 B2
(45) **Date of Patent: *Nov. 3, 2026**

(54) SENSOR FOR CONVERSION OF CHEMICAL AND/OR BIOCHEMICAL INFORMATION FROM AN ANALYTE

(71) Applicant: digid GmbH, Mainz (DE)

(72) Inventors: Malte Köhler, Mainz (DE); Nils Könne, Mainz (DE); Constantin Von Gersdorff, Mainz (DE); Konstantin Kloppstech, Mainz (DE)

(73) Assignee: digid GmbH, Mainz (DE)

( * ) Notice: Subject to any disclaimer, the term of this patent is extended or adjusted under 35 U.S.C. 154(b) by 577 days.

This patent is subject to a terminal disclaimer.

(21) Appl. No.: 18/236,709

(22) Filed: Aug. 22, 2023

(65) Prior Publication Data

US 2024/0060973 A1 Feb. 22, 2024

(30) Foreign Application Priority Data

Aug. 22, 2022 (DE) ........................ 102022121188.6

(51) Int. Cl.
*G01N 33/543* (2006.01)
*G01N 27/327* (2006.01)
*G01N 33/569* (2006.01)

(52) U.S. Cl.
CPC ..... *G01N 33/5438* (2013.01); *G01N 27/3275* (2013.01); *G01N 33/56983* (2013.01); *G01N 2469/20* (2013.01)

(58) Field of Classification Search
CPC ...... A61K 31/711; A61K 38/47; A61K 47/42; A61K 9/0019; A61K 9/127; A61P 11/06;
(Continued)

(56) References Cited

U.S. PATENT DOCUMENTS

2007/0033990 A1 2/2007 Grey et al.
2009/0139340 A1 6/2009 King et al.
2020/0215537 A1 7/2020 Ndieyira

FOREIGN PATENT DOCUMENTS

DE 60012962 U1 8/2005
DE 60023917 T2 7/2006
(Continued)

OTHER PUBLICATIONS

Rasmussen et al. "Cantilever surface stress sensors with single-crystalline silicon piezoresistors". Applied Physics Letters, Research Article May 12, 2005.

(Continued)

*Primary Examiner* — Jennifer Wecker
*Assistant Examiner* — Jonathan Bortoli
(74) *Attorney, Agent, or Firm* — ArentFox Schiff LLP

(57) ABSTRACT

A sensor is provided for conversion of chemical and/or biochemical information from an analyte in a sample to an electrical signal. The sensor includes a test cantilever having a base and a deformable part, with a receptor layer for selective uptake of the analyte applied at least atop the deformable part, with a first and second test transducer arranged atop the test cantilever, and a reference cantilever having a base and a deformable part, with a reference layer for selective non-uptake of the analyte applied at least atop the deformable part, with a first and second test transducer arranged atop the reference cantilever. The transducers output an electrical signal corresponding to the occurrence and/or the concentration and/or the amount of the analyte in the sample.

19 Claims, 12 Drawing Sheets

(58) Field of Classification Search
CPC .. A61P 25/18; A61P 25/24; A61P 3/10; A61P 31/10; A61P 31/12; A61P 33/02; A61P 33/10; A61P 35/00; A61P 5/06; A61P 9/06; A61P 9/12; G01N 2009/006; G01N 2291/0256; G01N 2291/0427; G01N 2469/20; G01N 27/3275; G01N 29/022; G01N 29/036; G01N 33/54373; G01N 33/5438; G01N 33/56983
See application file for complete search history.

(56) References Cited

FOREIGN PATENT DOCUMENTS

| | | | | |
|---|---|---|---|---|
| EP | 1226437 | B1 * | 8/2004 | ....... G01N 33/54373 |
| WO | 9709584 | A1 | 3/1997 | |
| WO | 0066266 | A1 | 11/2000 | |
| WO | 2005100965 | A1 | 10/2005 | |
| WO | 2006083566 | A2 | 8/2006 | |
| WO | 2007088018 | A1 | 8/2007 | |
| WO | 2017009868 | A1 | 1/2017 | |

OTHER PUBLICATIONS

Extended European Search Report in EP23192682.5, mailed Dec. 22, 2023, 6 pages.

* cited by examiner

SENSOR FOR CONVERSION OF CHEMICAL AND/OR BIOCHEMICAL INFORMATION FROM AN ANALYTE

CROSS-REFERENCE TO RELATED APPLICATION

This application claims priority to and benefit of German Patent Application No. 102022121188.6 filed Aug. 22, 2022, the contents of which are incorporated by reference in their entirety.

TECHNICAL FIELD

The present invention relates to a sensor for conversion of chemical and/or biochemical information from an analyte in a sample to an electrical signal in order thus to derive a qualitative conclusion as to the presence of the analyte in the sample and/or a quantitative conclusion about the analyte in the sample using the electrical signal generated.

BACKGROUND

The utilization of spring elements or cantilevers for detection of analytes in samples is known. In this case, the interaction of cantilevers with a sample liquid and the binding of the analyte in the sample to a coating of the cantilever is exploited in order to cause deformation of the cantilever. The deformation can then be used to infer the occurrence of the analyte via a strain gauge.

The deformation of cantilevers of different surface tensions is described, for example, in Rasmussen, P. A., Hansen, O., & Boisen, A. (2005) "Cantilever surface stress sensors with single-crystalline silicon piezoresistors" Applied Physics Letters, 86(20), 203502.https://doi.org/10.1063/1.1900299.

WO 2007/088018 A1 also proposes spring elements for use in biosensors, for example in DNA analysis.

However, the detection of an analyte in a sample may be found to be difficult because of large mechanical and thermal disruptive influences in the sample liquid and because of further chemical substances in the sample liquid. For that reason, it is necessary to filter out the components attributable solely to the interaction of the analyte with the cantilever from the actual measured signal.

SUMMARY

In view of the foregoing, it is an object of the present invention to provide an improved sensor for conversion of chemical and/or biochemical information.

The object is achieved by a sensor for conversion of chemical and/or biochemical information having the features of claim 1. Advantageous embodiments will become apparent from the dependent claims, the description and the figures.

Accordingly, a sensor for conversion of chemical and/or biochemical information from an analyte in a sample to an electrical signal is proposed, comprising a test cantilever having a base and a deformable part, with a receptor layer for selective uptake of an analyte in the sample applied at least atop the deformable part, with a first and second test transducer arranged atop the test cantilever, a reference cantilever having a base and a deformable part, with a reference layer for selective non-uptake of the analyte applied at least atop the deformable part, with a first and a second test transducer arranged atop the reference cantilever, wherein the transducers are formed and configured to output an electrical signal corresponding to the occurrence and/or the concentration of the analyte in the sample, wherein, by virtue of the selective non-uptake of the analyte by the reference layer, the interaction of the reference cantilever with the sample with the analyte corresponds to the interaction of the test cantilever with the sample without analyte. According to the invention, the test transducers are arranged on the deformable part of the test cantilever, and the reference transducers are arranged on the deformable part of the reference cantilever.

A sample here refers to a limited amount of a substance that has been taken from a greater amount of the substance, for instance from a reservoir, where the composition of the sample is representative of the composition of the substance in the reservoir and the corresponding occurrence in the reservoir can accordingly be inferred from the occurrence of the substance in and the substance compositions of the sample.

For example, a sample may be a saliva sample, or a blood sample, or a urine sample, or a swab, in particular a throat swab or a nose swab or a sinus swab, or extracted tissue. A sample in particular comprises any kind of biological sample, also including in particular samples from animals. A sample may also be a non-biological sample, for example a sample of a chemical substance.

In particular, one form of sample may be converted to another form of sample, such that the analyte, or its presence, can be detected in a simple and reliable manner. For example, a swab may be dissolved in a liquid, such that the swab dissolved in the liquid is then the actual sample. For example, the sample may be or comprise a lymph fluid or lymph.

The sample then contains the chemical information and/or the biochemical information about the analyte. An analyte here is the substance to be detected qualitatively and/or quantitatively in the sample or to be detected with the sensor. The analyte may in particular be present directly in the sample, or be dissolved in the sample, or adhere to the sample or to part of the sample, in particular to a sample particle. The analyte may also enter into a chemical, biological and/or physical interaction with the sample, such that the analyte is detectable only indirectly via a corresponding interaction.

The chemical information may include, for example, the type of the analyte, the concentration of the analyte, the occurrence of the analyte, the weight of the analyte, the reactivity of the analyte, the density of the analyte, etc. The biochemical information comprises the same properties as the chemical information, except that these substances may arise, for example, from biological processes. In particular, reference is made to biochemical information when the analyte has a particular effect on the biological cycle, for example metabolism or the immune system.

For conversion of the chemical and/or biochemical information from the analyte to an electrical signal, the sensor comprises a reference cantilever and a test cantilever. A cantilever here is a spring element that has a base and a deformable part.

The base here is an immobile part of the cantilever which is in particular fixedly bonded to the substrate and/or is supported by and/or has been elaborated from the substrate. The base of the cantilevers takes the form of a rigid base, such that only the deformable part of the cantilever is deformable.

The deformable part of the cantilever extends in longitudinal direction beyond the substrate on which the base is arranged. In other words, the deformable part of the cantilever is suspended on the base at one end and is not supported by the substrate. Because the deformable part projects beyond the substrate, the deformable part of the cantilever can be bent, deflected and extended. The spatial limit from which the cantilever is bendable or the cantilever transitions from the base to the deformable part is called the bending edge. The bending edge is usually an edge of the substrate when the cantilever protrudes beyond the substrate.

If the cantilever is deformed, this results in material stresses and forces in or on the cantilever material that can be measured. If such a material stress and/or force can be measured, it is possible to infer a deformation of the cantilever therefrom. A deformation may be a lifting or lowering deformation. The cantilever may alternatively itself deform, for example bend, corrugate or distort.

The deformation of the cantilevers can be brought about in a substance-specific manner by means of a suitable coating. For that reason, the reference cantilever has a reference layer for selective non-uptake of the analyte, whereas the test cantilever has a receptor layer for uptake of the analyte.

A receptor layer here is a substance that can interact with the analyte. This in turn means that the receptor layer is chosen specifically for each analyte. Analogously, a reference layer is a substance that cannot interact with the analyte. The reference layer too is therefore chosen specifically for the analyte.

What is meant in this case by interaction is that the analyte is in chemical and/or biochemical and/or physical interaction with the receptor layer. In particular, the interaction may consist in binding of the analyte to the receptor layer. An interaction may also consist in the absorption or adsorption or non-specific adhesion of the analyte to the receptor layer.

The receptor and reference layers are preferably chemically identical with regard to possible disruptive influences, and preferably differ solely by the interaction with the analyte. A substance that is not the analyte accordingly interacts just as strongly or just as weakly with the receptor layer as with the reference layer.

The effect of the selective uptake of the analyte on the test cantilever is that a force acts on the test cantilever as a result of the analyte, such that the test cantilever is sensitive to the analyte. Accordingly, the other substances in the sample that are not the analyte contribute merely to background noise in the form of background deflection of the test cantilever. The greater the concentration of the analyte in the sample or the faster the coverage of the cantilever surface with the analyte, for example, the faster and greater the increase in force on the test cantilever. A maximum force possible for the respective configuration is achieved when the cantilever is fully covered.

By contrast, the effect of the selective non-uptake of the analyte on the reference cantilever is that no force acts on the reference cantilever as a result of the analyte, such that only the substances that are not the analyte contribute to background noise in the form of background deflection of the reference cantilever.

This active force can bring about deformation in the deformable part of the test cantilever, while the deformable part of the reference cantilever is not deflected. The reason for the deflection of the cantilever is the change in surface tension caused by the interaction with the analyte. The change in surface tension leads to extension or contraction of the upper (or lower) surface of the cantilever. The different extension or contraction on the upper and lower sides results in an internal force or material stress in the material that leads to deformation.

Reference cantilevers according to the prior art merely have no receptor layer which is sensitive to the analyte. It is possible in this way to determine effects such as turbulence in the sample and thermal drift of the sensor system. However, with such a reference cantilever, the analyte can, for example, bind to the reference layer of the reference cantilever through non-specific binding. However, the analyte itself thereby contributes to the background noise. Therefore, in the case of a sensor according to the prior art, there is a need for reference measurements in a reference sample, i.e. a sample without analytes. Only in this way, the effect of the non-specific binding of the substances that are not the analyte can be established.

In the sensor proposed, the selective non-uptake of the analyte by the reference cantilever significantly simplifies the test method, since the reference cantilever is not sensitive to the analyte, and therefore the analyte does not contribute to the background noise either. Only the substances that are not the analyte contribute here to the background noise of the reference cantilever. The selective non-uptake of the analyte on the reference cantilever may be brought about to some degree in that the reference cantilever is exposed to the same turbulences, the same thermal drift and the same influence of all substances that are not the analyte as in a reference sample. The difference is, however, that the reference signal is determined directly in the sample liquid.

In particular, a reference cantilever with reference layer and a test cantilever with receptor layer results in distinctly more specific analysis of the analyte than just a reference cantilever without receptor layer, since both the reference layer and the receptor layer have a specific interaction or non-interaction with the analyte.

The structure of the sensor with reference cantilever and test cantilever has the advantage that two measurements can be undertaken simultaneously in the sample, and the measurement by the reference cantilever can calibrate the measurement by the test cantilever. This makes it possible to reduce environmental influences, for instance chemical, thermal, mechanical, electrical and fluidic disruptive influences, on the respective measurement, such that occurrence of the analyte can be inferred from the comparison of the measurement on the test cantilever and on the reference cantilever.

These forces or material stresses, for example extensions or contractions, that act on the cantilever can ultimately be detected by the transducers, and stresses of different magnitude are detected by the transducer through extensions or contractions of different magnitude.

The transducers accordingly have the purpose of determining or of measuring the deformation of the cantilevers. According to the invention, the transducers are arranged on the deformable parts of the cantilevers. For example, a deformation of the cantilever may have the effect that the resistance of a transducer rises or falls, while no deformation of the cantilever causes no change in the resistance of the transducer either. This can be achieved, for example, via a configuration of the transducers in accordance with the principle of a strain gauge, as a result of which a deformation of the respective cantilever is manifested in a change in length of the transducer strain gauge applied thereto, and hence it is possible to detect a deformation of the cantilever directly by a change in the resistance of the strain gauge.

The chemical and/or biochemical information from the analyte is thus detectable via a deformation of the cantilever, subsequent registration via a transducer, and finally via a change in an electrical property of the transducer.

Because the first and second test transducers are arranged on the deformable parts of the test cantilever and the first and second reference transducers are arranged on the deformable part of the reference cantilever, it is possible to find a measure of extension of the test transducer that corresponds to the strength of the interaction of the analyte with the deformable part of the test cantilever.

For example, the first reference transducer of the reference cantilever, influenced by the environmental conditions and interacting with the sample, can cause a first electrical reference state of the first reference transducer, while the interaction of the test cantilever with the environmental conditions of the sample causes a first electrical test state of the first test transducer.

For example, the reference cantilever can be bent by a first amount by the influence of the environmental conditions, such that the deflection in the first reference transducer causes a first electrical reference state and that in the second reference transducer causes a second electrical reference state. The test cantilever is bent by a second amount by the influence of the environmental conditions and bend by a third amount by the additional interaction with the analyte in the sample, which causes a first electrical test state in the first test transducer and causes a second electrical test state in the second test transducer.

Comparison of the electrical states of the first and second transducers gives a measure of the deformation of the cantilevers. At the same time, comparison of the respective first transducers and/or of the respective second transducers gives a measure of the difference in deformation of the cantilevers. This makes it possible to infer a specific influence of an analyte on the test cantilever.

The configuration with four transducers has the advantage that such local calibration of the sensor is possible at the site of influence of the sample and of the analyte.

The force to be detected may be a bending force and/or an extension force and/or a shear force and/or a contraction force and/or be based on the flexural stiffness of the reference cantilevers and test cantilevers.

A bending force may bring about a change in the geometry of the cantilever, in particular impose a curvature on the cantilever that differs from the unstressed cantilever.

An extension force or contraction force may especially cause a change in length of the cantilever. The respective change in length may be different depending on the direction of the crystal lattice of the cantilever.

The extension (or contraction) on the upper surface may in particular be different from the lower surface of the cantilever. The extension of the upper surface may in particular occur parallel to the base of the cantilever (called a transverse extension) or perpendicular to the base of the cantilever (called a longitudinal extension). The magnitude of the extension here is strongly dependent on the geometry and the crystal structure of the cantilevers and of the other layers provided on the surfaces, for example the electrodes, such that optimal detection of the analyte can be achieved by optimization of alignment and cantilever geometry.

If the extension force is different on the upper surface and the lower surface, the acting force is also referred to as shear force.

In the case of a deflected cantilever, a bending force is active, since a curvature is imposed on the cantilever. This extends the upper surface of the cantilever, and this extension is in particular greater than on the lower surface of the cantilever, such that an overall shear force acts on the cantilever.

The abovementioned forces are all based on what is called the modulus of elasticity of the cantilever. The modulus of elasticity of the cantilever is a material constant that is specific to the material used for the cantilever. By choice of the material or material composition or by processing the material, it is possible to set the modulus of elasticity within a particular range, such that the effect to be measured can be optimized for the respective transducer setup. Conversely, it is of course also possible to adapt the transducers to the existing modulus of elasticity of the material and to optimize their sensitivity.

The cantilevers may preferably be what are called bimaterial cantilevers, for example cantilevers made of a gold layer and a silicon nitride layer. A bimaterial cantilever consists of material layers that together have a defined state of stress. For example, the state may be stress-free, such that the intrinsic mechanical stresses are minimal. It may alternatively be the case that a bimaterial cantilever is prestressed, such that the cantilever is particularly sensitive to a change in surface tension. It may alternatively be the case that a homogeneous cantilever is coated differently on the upper side and the lower side in order to imitate the described bimaterial effect. In particular, it is possible to use isotropic and anisotropic materials for cantilevers in order thus to achieve optimization of the longitudinal and transverse extension. For example, an isotropic metal may be used on an anisotropic substrate.

The deformable parts of the reference and test cantilevers may have identical geometric dimensions, where the width of the deformable part of the reference and test cantilevers preferably corresponds to the length of the deformable part of the reference and test cantilevers, where the deformable parts of the reference and test cantilevers more preferably have a width of less than 200 μm, a length of less than 200 μm and a thickness of less than 1 μm, in particular a width of 50 μm, a length of 50 μm and a thickness of 0.3 μm or a width of 125 μm, a length of 20 μm and a thickness of 0.1 μm.

This makes it possible to generate a particularly large force on the transducers through the deformation of the cantilevers.

The deformable parts of the cantilevers may, for example, rather than a rectangular geometry, also have a different geometry. For example, the cantilevers may have a V-shaped geometry or have a triangular geometry. In particular, it is also possible that the cantilever is not a closed body but has holes or recesses, for example.

The reference and test cantilevers may comprise $Si_3N_4$ and/or $SiO_2$ and/or $Si_3N_4/SiO_2$ and/or SiC and/or Si and/or aluminium oxide or consist of Si or comprise at least one polymer. The bases or the overall base may equally also comprise the materials mentioned. The bases and the reference and test cantilevers may also be produced in one piece collectively from the materials mentioned by conventional production processes as known in the processing of wafers.

The silicon-based reference and test cantilevers make it possible to use production methods known from the semiconductor industry, thus enabling the production of sensors according to the invention on a large industrial scale. Polymers can likewise be produced on a large industrial scale and have the advantage that their material properties can be predetermined to a large degree.

The transducers may have identical intrinsic physical properties, where the transducers are configured to adjust their electrical properties, preferably the electrical resistance or another value proportional to the k value, according to the forces acting on the reference and test cantilevers.

The k-value, also called gauge factor, is the proportionality constant between the extension of the transducer and its change in resistance:

$$\frac{\Delta R}{R} = k\frac{\Delta L}{L},$$

where ΔR is the change in resistance of the transducer, R is the resistance of the transducer when the cantilever is not bent, ΔL is the change in length of the transducer and L is the length of the transducer when the cantilever is not bent. In particular, it is also possible to measure any other measured variables proportional to the k value or to resistance, for example conductivity.

Identical intrinsic physical properties here include those properties that are responsible for the measurement properties of the transducer on a cantilever. This relates more particularly to the resistance or conductivity of the transducer. The resistance depends in particular on the geometry of the transducer, such that, in the case of uniform conductivity of the various transducers, the geometry of the transducers accordingly has to be identical. In particular, each transducer should react equally to an equal active force or deformation of the cantilever.

The intrinsic physical properties are defined in particular by the nanostructure of the transducers. A reliable production process for the transducers thus makes it possible to ensure that all transducers react identically to a force, such that variances between the various measured forces are based solely on the external action on the cantilevers and do not depend on the intrinsic physical properties.

The reference and test cantilevers, and the first and second reference and test transducers, may be in a mirror-symmetric arrangement relative to one another.

A mirror-symmetric structure makes it possible to reduce outside disruptive influences on the transducers, or at least to guide them symmetrically to one another. This can improve measurement accuracy and susceptibility to faults.

The sensor may have electrodes, preferably four electrodes, that are configured to make electrical contact with the transducers.

An electrode here is a conductive layer, for example made of gold, or a wire or cable which, from a connection end of the transducer, can make an electrically conductive connection to an external device, for example a current or voltage source, or to a corresponding measurement device. In principle, any conductive connection between the transducer and the external device may be regarded as an electrode. However, in particular the part of the electrical connection that is formed on the sensor is considered here to be an electrode.

An electrical connection is typically made from the sensor to an external source or a measurement device via an electrical terminal. In this case, an electrical terminal plug is contacted by a cable or a wire to what is called a bonding pad, for example in that the wire is fixedly ultrasonically welded thereto. An electrical connection then leads directly from the bonding pad to the transducer. The electrical isopotential surface between the transducer and the bonding pad is called electrode hereinafter.

The electrode serves to make electrical contact with the transducers and in particular to make it possible to route the electrical signals from the sensor to a measuring device.

The electrodes may in particular be at different electrical potentials and interact with one another thereby. In order to minimize this mutual influencing of the electric currents and voltages in the electrodes, it is therefore advantageous for the electrodes likewise to have a symmetrical form such that the respective interference is at least distributed uniformly throughout the system. This can in particular be achieved by using an even number of electrodes or using only four electrodes in the case of four transducers.

Due to the configuration of the electrode geometry, it is therefore possible for the basic signal level that arises at the electrodes due to any potential differences to be less than 1.1 V, such that it is not necessary to electrically encapsulate the electrodes. Electrical encapsulation may be understood here to mean, for example, electrical insulation or covering or shielding of the electrodes and of the bonding wires. The production process may thereby be simplified, and measurement accuracy is improved.

The transducers may be electrically interconnected in a full bridge, where the full bridge is configured to establish a cross-bridge voltage based on the electrical properties of the transducers, in particular in the event of an asymmetric change in the electrical properties of the transducers.

A full bridge here is a measuring apparatus for measuring electrical resistances or small changes in resistance. A full bridge is also known by the names Wheatstone bridge or H-bridge or symmetrical full bridge or thermo-symmetrical full bridge.

In the ground state of the full bridge of the sensor, the cross-bridge voltage is ideally equal to zero, since an equal force is acting on all the transducers involved. This ground state is preferably established at the early stage of the production process, such that only a small offset voltage that can be compensated for by means of a measurement setup is established between the electrodes.

Proceeding from this ground state of full bridge, asymmetric changes in force can then preferably be detected. If, for example, the first test transducer of the test cantilever reacts to an exerted force with a change in its electrical property, or with a change in its electrical resistance, the ratio of the resistances in the full bridge is no longer balanced, such that a cross-bridge voltage is established. The cross-bridge voltage established can ultimately be detected with a measurement device.

By virtue of implementation as a full bridge, calibration of the test transducer of the test cantilever is effectively brought about via the reference transducer of the reference cantilever.

The sensor may comprise a cross-bridge voltage detector configured to detect the cross-bridge voltage of the full bridge, wherein the detected cross-bridge voltage is used to infer the occurrence of the analyte selectively taken up by the receptor layer, preferably to infer the magnitude or concentration of the occurrence.

A cross-bridge voltage detector may in particular be any detector capable of detecting a voltage. For example, this may be a measuring resistor, or a signal transmitter or a measuring device that indicates the voltage, or another type of detector that generates an output signal by detecting a voltage. In particular, the cross-bridge voltage detector may take the form of an A/D converter and convert the cross-bridge voltage to a digital value.

The change in the cross-bridge voltage is ideally expressed as a ratiometric change in relation to a defined, i.e. measured, supply voltage. For example, a drift in the supply voltage then does not influence the measured signal.

The first and second test transducers may each be arranged in one depression or be arranged in a common depression in the test cantilever, and the first and second reference transducers may each be arranged in one depression or be arranged in a common depression in the reference cantilever.

A depression here may, for example, have a rectangular cross section in thickness direction of the cantilever and/or have a rectangular cross section in length direction of the cantilever. It may also be the case that the depression has, for example, a partly elliptical or round cross section.

A depression here may accommodate a transducer, such that the transducer is arranged in the depression. In particular, the transducer may fill the depression, such that the volume of the depression is filled completely by a transducer. It is also possible that the transducer fills merely part of the volume or that the transducer is arranged merely on one side of the depression, for example on the bottom side of the depression. The bottom side here is the side offset from the surface of the cantilever.

The depressions in the test cantilever and in the reference cantilever can increase the elasticity of the test cantilever and of the reference cantilever locally at the site of the transducers.

The reason for this is that the material of the cantilevers is thinned out.

The test transducers in the depressions in the test cantilever can reduce the extensibility of the test cantilever, and the reference transducers in the depressions in the reference cantilever can reduce the extensibility of the reference.

To some degree, the transducers are the antagonists of the depressions and bring about a reduction in extensibility. For that reason, transducers applied merely atop the surface of a cantilever bring about a decrease in extensibility and hence a decrease in measurement sensitivity.

The transducers arranged in the depressions of the cantilevers, however, detect the extension of a cantilever having high extensibility, such that high measurement sensitivity can be achieved. At the same time, however, the transducer should be arranged at a distance from the neutral axis in order to achieve any measurement sensitivity at all. Accordingly, the neutral axis preferably does not intersect with the transducer, but lies outside the neutral axis.

The enhanced measurement sensitivity can be explained mathematically as follows. For thin and broad cantilevers, the mechanical stress a of the cantilever is defined by $$\sigma = \frac{My}{I}$$

where M is the bending moment for example generated by the chemical interaction, and y is the distance from the neutral axis of the cantilever. The neutral axis here is the axis along which the stresses present in the material are just eliminated. In particular, all layers of the cantilever are taken into account here, including activation and passivation layers. For thin and broad cantilevers, the second area moment I, for example, is given by $$I = \frac{bh^3}{12}$$

where b is the width of the cantilever and h the thickness of the cantilever. At the same time, the extension of the cantilever is given by:

$$\epsilon = \frac{\sigma}{E}$$

where E is Young's modulus. Inserting the above equations gives the extension of the cantilever as a function of the distance from the neutral axis:

$$\epsilon = \frac{12My}{Ebh^3}.$$

Reducing the distance y of the transducer from the neutral axis with constant Young's modulus E results in a drop in extension and hence also in the sensitivity of the cantilever. However, the lower stiffness of the cantilever, by virtue of the lower thickness, more than compensates for the low elongation, and so a particularly high sensitivity of the cantilever is achieved.

At least one depression may have a depth of more than 5%, preferably more than 20%, more preferably more than 50%, of the thickness of the cantilever.

The deeper the depression, the more elastic the cantilever becomes. For example, the cantilever may have a thickness of 500 nm, such that the depression may have a depth of more than 25 nm, preferably more than 100 nm, more preferably more than 250 nm.

The distance of at least one transducer from the neutral axis of the cantilever may be less than 20%, preferably less than 10%, more preferably less than 5%, of the thickness of the cantilever. The smaller the distance, the greater the measurement sensitivity.

The height of at least one transducer may correspond at least to the depth of the depression.

In particular, the upper side of the transducer may conclude with the surface of the cantilever. It may alternatively be the case that the upper side of the transducer lies above the surface of the cantilever. In that case, however, the electrical connection may be undertaken over the cantilever edge.

The choice of thickness of the transducer can in particular result in adjustment of the stiffness of the cantilever.

The depressions may be arranged on the upper and/or lower surfaces of the cantilever.

By means of depressions on the upper and/or lower surface, it is in particular possible to detect different bending moments, such that a particularly large measurement signal is generated by the transducers.

By contrast with the prior art, the transducer is thus not thinned in order to maintain or to reduce the elasticity of the cantilever in spite of transducers arranged thereon, in order to obtain a maximum measurement signal. Instead, the cantilever is thinned here in order to minimize the distance from the original neutral axis, in order to obtain a maximum measurement signal.

The first and second transducers may be configured to detect different force components.

In dependence on the orientation of the transducers relative to the cantilever axes, in particular relative to the longitudinal axis, the width axis and the thickness axis of the cantilever, different forces are active.

For example, a transducer on the upper surface of the cantilever detects extension, while a transducer on the underside of the cantilever with the same bending of the cantilever detects contraction. For example, a transducer on the upper surface can detect transverse extension along the width axis of the cantilever, and a further cantilever longitudinal extension along the longitudinal axis of the cantilever.

In particular, the detection of different force components can be utilized to increase the signal spread between the first and second transducers of a cantilever. This can generate a particularly large measurement signal.

For example, the first and second transducers may be aligned identically or differently with regard to the longitudinal axis of the transducers. In particular, the first and second transducers may be aligned at an angle to one another, preferably aligned orthogonally to one another.

For example, a first transducer may be aligned at an angle of 20° to the longitudinal axis and the second transducer may be aligned at an angle of 40° to the longitudinal axis.

For example, a first transducer may be aligned at an angle of 45° or 60° or 90° to the second transducer.

For example, the first transducer may be aligned along the longitudinal axis of the cantilever, and the second transducer may be aligned perpendicular to the longitudinal axis of the cantilever.

For example, the first transducer may be aligned along the longitudinal axis of the cantilever, and the second transducer may likewise be aligned along the longitudinal axis of the cantilever.

For example, the first transducer may be aligned perpendicular to the longitudinal axis of the cantilever, and the second transducer may likewise be aligned perpendicular to the longitudinal axis of the cantilever.

For example, the first and second transducers may be rectangular. For example, the longitudinal axis of the first transducer may be aligned at an angle of 0° to the longitudinal axis of the cantilever which is perpendicular to the bending edge, while the longitudinal axis of the second transducer is aligned at an angle of 90° to the longitudinal axis of the cantilever. This allows the first transducer to detect a longitudinal extension, while the second transducer detects a transverse extension. It may be the case that the longitudinal extension of the cantilever is positive, while the transverse extension of the cantilever is negative. In that case, the signal spread is particularly large and particularly simple to detect.

The first transducer may be arranged at the site of maximum surface tension of the cantilever, and the second transducer may be arranged at the site of minimum surface tension of the cantilever.

The site of minimum surface tension may especially be the site of the most negative surface tension.

This can likewise generate a particularly large measurement signal. For example, the first transducer can measure a positive longitudinal extension on the upper surface of the cantilever, and the second transducer can measure a negative longitudinal extension on the upper surface of the cantilever.

It can also be the case that both transducers are arranged on the same surface, of the sites of longitudinal extension and of transverse extension on the cantilever are different.

Comparison of the two measurement signals between reference cantilever and test cantilever can thus create a particularly large measurement signal.

The upper surfaces of the reference and test cantilevers may be activated by an activation layer, where the activation layer is configured, in the event of a force exerted on the reference and test cantilevers, to provide a greater surface extension by comparison with the non-activated lower surface of the reference and test cantilevers, and where the activation layer comprises gold or other chemically inert materials. However, it is also possible to activate the lower surface, which merely reverses the description of the upper and lower surfaces.

Activation of the upper surface may mean that applying an activation layer provides promotion of adhesion for a further layer. The reason for this may be that the base material of the cantilever, for example, does not bind to the further layer, in particular the reference layer.

In particular, the activation layer may comprise gold, or consist entirely of gold.

The complete surface of the cantilevers is preferably coated with gold, since the receptor layer is preferably formed atop the gold layer. Accordingly, an expansive layer comprising the activation layer may also result in coverage of a greater area with the receptor layer, so as to give a large detector area for the analyte. The large detector area for the analyte in turn results in a particularly large deformation of the cantilever, such that sensitive detection of the occurrence of the analyte is possible.

It is also possible that only the deformable part of the cantilevers is covered with gold, especially covered with gold up to the bending edge.

Because the upper surface has an activation layer, the structure of the cantilevers is in particular non-homogenous or asymmetric in terms of height, and instead consists of layers. This can have a major effect on the elasticity of the cantilever, so as to give rise to a greater surface extend on the upper surface in the event of deformation of the cantilevers, which in turn leads to a greater measured signal.

Because of the good conductivity, the coating of the cantilevers with gold may likewise be used to form electrodes for the transducers. For this reason, the distance between the electrodes may also be minimized, since the smallest possible area of the cantilever is thus not coated with gold. A large detector area may accordingly be chosen.

The activation layer may in particular also consist of or comprise a chromium-gold alloy, since this influences the mechanical properties of the cantilever to a lesser degree. The inclusion of chromium in particular achieves homogeneity of the crystallites of the gold layer, such that any disruptive anisotropic effects can be avoided by the crystal lattice of a hypothetical crystalline layer.

It is also possible that the activation layer consists of or comprises a titanium-gold alloy.

The lower surfaces of the reference and test cantilevers may be passivated by a passivation layer, where the passivation layer is configured to minimize non-specific protein adhesion on the reference and test cantilevers, and where the passivation layer comprises trimethoxysilane and/or a blocking substance.

Unlike an activation layer, a passivation layer is a layer intended to minimize or prevent any interaction between the cantilever and another material. This means that, during the production of the receptor layer, this binds only to the upper surface of the cantilever and not to the lower surface of the cantilever. The binding of the receptor layer to an analyte thereby makes it possible to achieve a greater surface tension on the upper surface. This further increases the asymmetry of the layer structure, which can lead to improved extension properties for the signal detection.

Suitable materials for the passivation of the lower surface are in particular trimethoxysilane, and what are called blocking layers. This passivation layer minimizes what is called non-specific protein adhesion. Protein adhesion is adhesion of a protein to the surface. Non-specific adhesion of a protein or of a substance in general to the cantilever may lead to distortion of the measurement result, since these non-specific substances likewise interact with the cantilevers. By preventing this non-specific adhesion, the relative influence of the intended specific adhesion or interaction of the analyte with the cantilever relative to the basic state of the cantilever is increased.

However, it is also possible for a passivation layer also to bind the analyte, but in such a way that the resulting surface tension on the lower side is the opposite of the surface tension of the activation layer on the upper side. This makes it possible to achieve greater deformation of the cantilevers.

What is call the blocking layer may in particular be adapted to the respective analyte under investigation and preferably also to the particular solution in which the analyte is present, in order to define a measurement window for the analyte. The blocking layer is applied here in what is called the spotting process or washing process.

In the washing process, what is called a "sealer" protects the hydrate shell of the detector proteins during drying and thus makes them storable, in particular storable at room temperature without cooling. The sealer is incorporated in a matrix in soluble form, such that it is soluble for a sample liquid such as water. The sealer additionally has a certain layer thickness, such that the cantilevers are mechanically stabilized, which increases protection during storage of the cantilevers. A sealer may for example contain sugar. Sugar crystals are hydrophilic and therefore protect the hydrate shell of the proteins. A so-called reconstitution of the proteins, in which the dried proteins are reactivated in the measurement liquid, is thus possible.

In the case of spotting of the receptor proteins, what are called "buffers" are used in order to enable reconstitution of the proteins in the sample liquid. Here too, the storability of the sensors is increased by drying.

The reference cantilever and the test cantilever may be of chemically identical structure.

In this case the measured signal, in particular in the case of a differential measurement of cross-bridge voltage, is based solely on the influence of the analyte on the cantilevers and is not caused by further properties of the cantilevers.

In particular, the basis of chemical identity is that the cantilevers are changed and adapted to the extent that they differ only in terms of their binding properties or interaction properties with respect to the analyte to be analyzed. For all further substances, the intention is to achieve very substantially identical interaction, or minimum interaction.

For this purpose, the reference cantilever and the test cantilever have an identical layer structure that differs only in that a receptor layer has been applied to the test cantilever and a reference layer to the reference cantilever. In particular, chemical identity thus means that the two cantilevers differ only in the reference/test layer.

The overall layer structure of the cantilevers described above can also be inverted. This means that the reference and receptor layers, rather than being applied to the upper surface, may also be applied to the lower surface of the cantilevers. For example, the receptor layer may also be arranged on the lower side of the cantilever.

In order that the cantilever deforms, any chemical binding to the cantilever should ideally be on a single side, or the sign of chemical binding on the upper side and lower side should differ. When the analyte binds to the upper side, there should not be any non-specific binding to the lower side of the cantilever, since otherwise the surface tension that results from the chemical binding of the analyte may be compensated for by the non-specific chemical binding to the lower side of the cantilever.

In other words, the chemical binding to the upper side and the lower side must be at least asymmetric in order to achieve a deformation. Stronger binding to the upper side than to the lower side or stronger binding to the lower side than to the upper side accordingly leads to a measurable deformation of the test cantilever.

The reference and test cantilevers may have a further layer that comprises a self-assembly monolayer.

A self-assembly monolayer may in particular reduce unevenness on the gold surface, such that a uniform coating of the cantilevers with the receptor layer or reference layer is possible. The homogeneous surface properties of the cantilevers thus ultimately make it possible to improve the binding properties of the receptor layer and of the analytes.

The receptor layer may comprise antibodies for an antigen and the reference layer may comprise an antigen-specific isotype control antibody targeting the antibody of the reference layer.

Antibodies are, for example, proteins that are produced by body cells as a reaction product to antigens. Antibodies are typically used by the human immune system to bind to the antigens of viruses, such that the viruses are marked and an outbreak of a viral infection can be avoided by the immune system. However, there are also antibodies that bind to non-immunological substances, for example THC. It may in particular be the case that an antibody binds to different antigens, such that the specificity of the antibody is lowered.

By contrast, an isotype control antibody specifically does not bind to the antigen of a virus, such that, in the event that there is simultaneously binding of the antibody to the antigen and of a non-binding isotype control antibody to the antigen with high specificity, the presence of a particular virus or antigen of a virus may be inferred.

The antibody of an antigen may be part of the receptor layer of the test cantilever, while the isotype control antibody of the antigen may be part of the reference layer. This has the advantage that deflection of the test cantilever can be confirmed simultaneously by non-deflection of the reference cantilever.

For better adhesion of the antibodies, the reference layer and receptor layer of the cantilevers may additionally include what is called protein A, which binds covalently to the self-assembly monolayer.

The layers may be produced in a dipping/spotting process, where the spotting may preferably be performed by means of commercially available machines. Droplets of the respective layer are deposited here on the cantilever, so as to spatially delimit the functionalization, which in particular enables inexpensive and independent coating of the cantilevers. The very small drops are prevented from drying by appropriately controlling the environmental parameters, such as temperature, air humidity and dew point. The lower sides of the cantilevers are not activated here, and so the antibodies used come into contact merely with the upper surface of the cantilever. The layers are then dried, such that a higher or lower temperature has little or preferably no influence on the antibodies. This allows a long shelf life, in particular in an inert gas. The protein layers are in particular applied after the transducers have been applied, but before the sensors or chips are singularized from the wafer.

The receptor layer can generally provide molecule-specific binding forces, and the reference layer provides no molecule-specific binding forces. It is thereby possible to detect a particular molecular species.

The receptor layer may comprise single-strand DNA (ssDNA) and/or other DNA fragments that are able to bind specifically to DNA fragments in the sample. The reference layer may comprise single-strand DNA and/or other DNA fragments that do not bind to chemical and/or biochemical and/or physical species in the sample, but correspond to the receptor layer in terms of characteristic parameters (for example chain length, chemical structure).

The receptor layer may comprise single-strand RNA and/or other RNA fragments that are able to bind specifically to RNA fragments in the sample. The reference layer may comprise single-strand RNA and/or other RNA fragments that do not bind to chemical and/or biochemical and/or physical species in the sample, but correspond to the receptor layer in terms of characteristic parameters (for example chain length, chemical structure). It is thereby possible to detect a particular DNA or RNA and their fragments and/or other oligonucleotides.

The receptor layer may comprise antibodies and/or other and/or further proteins that are able to specifically bind target proteins, and the reference layer may accordingly comprise specific isotype control antibodies and/or further proteins that do not bind to chemical and/or biochemical and/or physical species in the sample.

The receptor layer may comprise scFv antibodies, and the reference layer may comprise scFv antibody-specific isotype control antibodies. An scFv antibody is an artificially produced antibody fragment. Because an antibody can be broken down into multiple fragments, the reactivity of the sensor to a low sample concentration may be increased. For example, the scFv antibody may be in a F(ab) or a $F(ab')_2$ or a F(ab') configuration.

The receptor layer and/or the reference layer may comprise hydrogels.

Hydrogels are molecular matrices that have very good ability to bind water and swell up significantly on contact with water. By chemically modifying the hydrogels, in particular the matrix, it is possible to bring about a strong reaction of the hydrogel to the presence of antibodies, such that the mechanical deformation of the cantilever is multiplied. It is thus in particular also possible to perform a pH-sensitive measurement of the analyte.

BRIEF DESCRIPTION OF THE DRAWINGS

Preferred further embodiments of the invention are elucidated in detail by way of the description of the figures that follows. The figures show.

DETAILED DESCRIPTION

Figure 1:
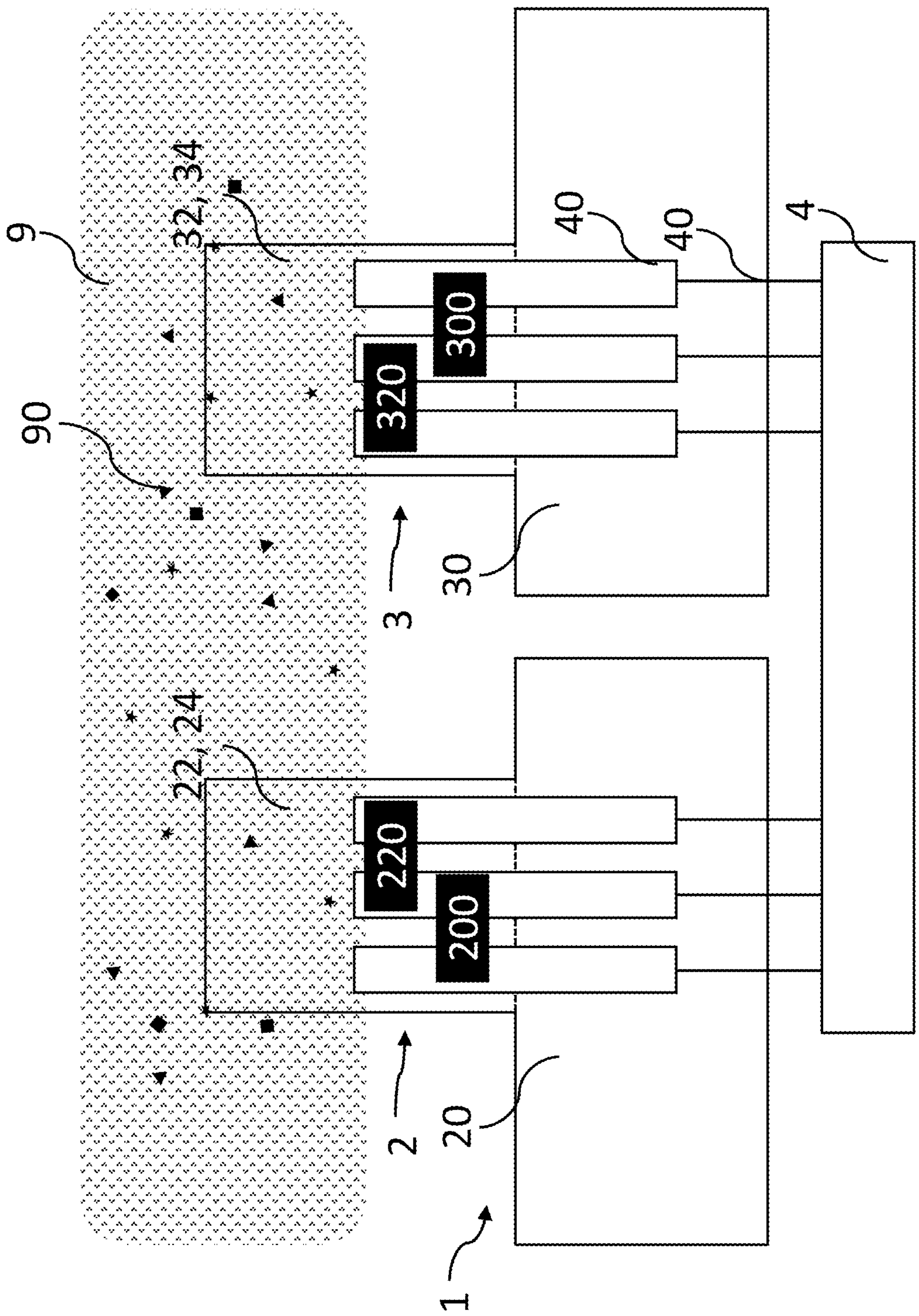
FIG. 1 is a schematic diagram of the sensor.

Exemplary embodiments are described below with reference to the figures. Elements that are identical, similar or have the same effect are given the same reference numerals here in the various figures, and repeated description of these elements is omitted in some cases in order to prevent redundancy.

FIG. 1 shows a schematic of a first embodiment of the proposed sensor 1 for converting chemical and/or biochemical information. The sensor 1 comprises a test cantilever 2, which has a base 20 and a deformable part 22. Arranged atop the deformable part 22 are a first test transducer 200 and a second test transducer 220. Analogously, the sensor 1 also has a reference cantilever 3, which in turn has a base 30 and a deformable part 32. Arranged atop the deformable part 32 are a first reference transducer 300 and a second reference transducer 320.

The transducers 200, 220, 300, 320 are each connected, via electrodes 40, to electronics 4 that are capable of recording or of forwarding the measured signals from the transducers 200, 220, 300, 320, while the electronics 4 are likewise capable of supplying the transducers 200, 220, 300, 320 with current and/or voltage.

The sensor 1 has the function of indicating the occurrence and preferably the amount of an analyte 90 in a sample 9. In FIG. 1, the sample 9 is a liquid, for example lymph or a diluted lymph fluid. Alternatively, the sample 9 may be saliva or blood or another body fluid. It may also be the case that the sample 9 stems from a tissue sample or has been obtained and/or synthesized from another sample taken. The analyte 90 may be dissolved here in the sample, or be in undissolved form, as a suspension or dispersion or emulsion.

In any case, the sensor 1 should be used to examine the sample 9 for the occurrence and/or a concentration and/or an amount of the analyte 90. For this purpose, a receptor layer 24 is applied to the test cantilever 2, with which an analyte 90 can interact, or a receptor layer 24 that can adsorb or absorb the analyte 90.

The interaction alters the surface tension of the section, coated with the receptor layer 24, of the deformable part 22 of the test cantilever 2 changing, which leads to deformation of the deformable part 22 of the test cantilever 2. The first and second test transducers 200, 220 therefore also register a deformation of the deformable part of the test cantilever 2, which is in turn interpreted in the electronics 4 as the measured signal.

However, even the interaction with the sample liquid 9 can result in registration of deformation by the test transducers 200, 220, for example in that merely the surface tension of the liquid acts on and bends the deformable part 22 of the test cantilever 2. The presence of an analyte 90 is accordingly not responsible for such a deformation.

In order to establish the magnitude of this basic effect of the sample 9 on the test cantilever 2, the reference cantilever 3 is brought into contact with the sample 9 at the same time as the test cantilever 2. For this purpose, the reference cantilever 3 has a reference layer 34 with which an analyte 90 cannot interact. This enables differentiation from the measurement signal from the test cantilever 2. There will accordingly be a difference in the measured signals from the transducers 200, 220, 300, 320 if an analyte 90 occurs in the sample 9.

However, the test cantilever 2 and the reference cantilever 3 are at different positions in the sample 9, such that different ambient conditions, for example fluctuations in temperature or concentration gradients etc., can influence measurement accuracy.

However, these different ambient conditions can be corrected for by a comparison of the measured values from the transducers 200, 220, 300, 320. The sensor 1 can accordingly be used to analyse the occurrence of an analyte 90 in a sample 9 in isolation, since the influence of interactions that are not associated with the analyte 90 is reduced and isolated due to a multitude of measurement points on the reference and test cantilevers 3, 2. This enables high measurement accuracy of the occurrence of the analyte 90 in the sample 9. The magnitude of the difference of the measured signals from the transducers 200, 220, 300, 320 of the test cantilever 2 and of the reference cantilever 3 can thus be used in the simplest case to directly infer the amount of occurrence of the analyte 90 in the sample 9.

Figures 2A, 2B:
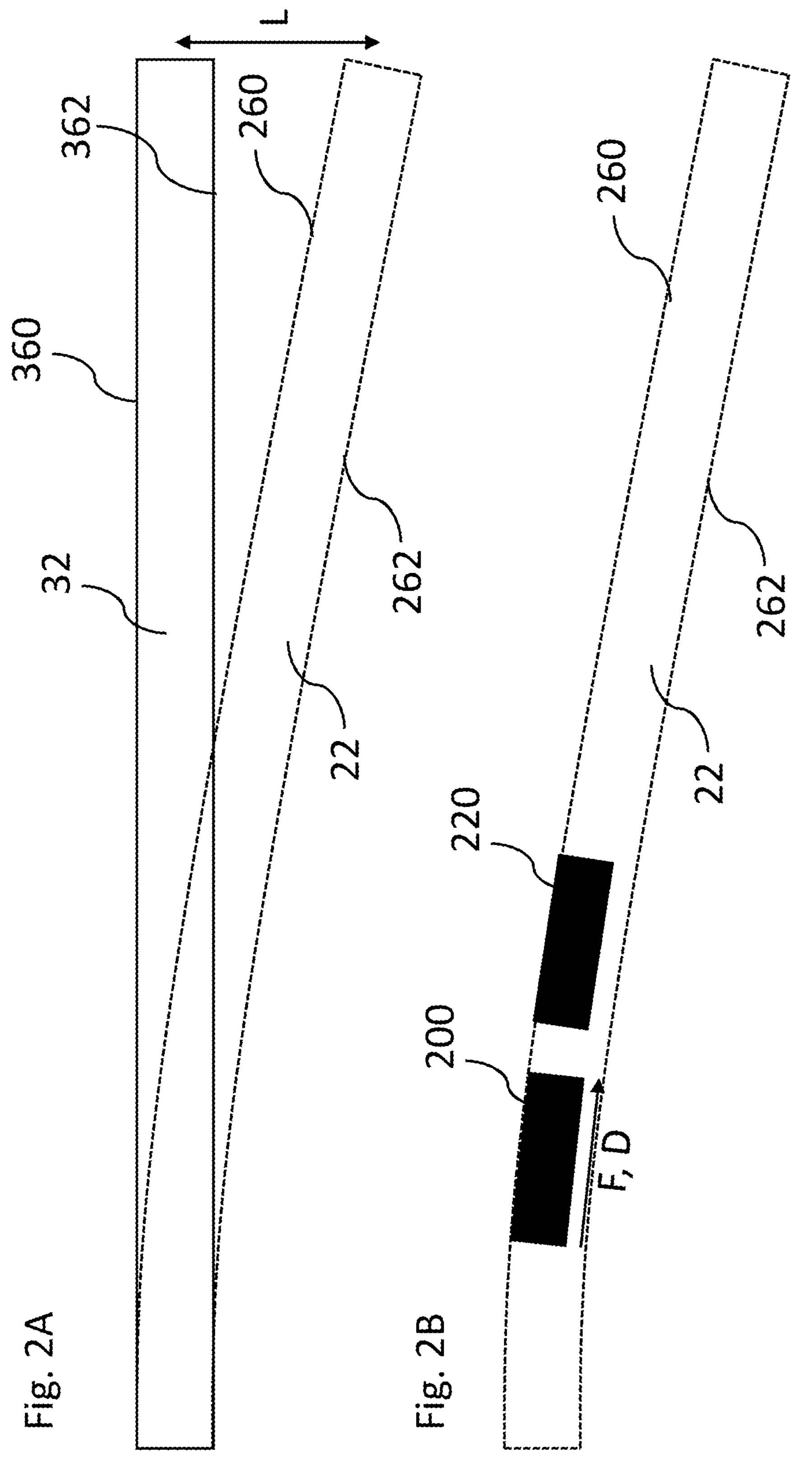
FIG. 2A-2F are schematic diagrams of the sensor with various depressions.

FIG. 2A shows the comparison of the deformable parts 32, 22 of the reference and test cantilevers 3, 2 in the event of a deformation and longitudinal extension. The deformable part 32 of the reference cantilever 3 has an upper surface 360 and a lower surface 362. The deformable part 22 of the test cantilever 2 likewise has an upper surface 260 and a lower surface 260. If an analyte 90 of the sample 9 interacts with the test cantilever 2, or with the receptor layer 24, the deformable part 22 deforms from the fixed part (that transitions into the base of the test cantilever) toward the freely mobile part of the deformable part 22. The depicted deflection L results from the relative deflection between the deformable part 32 of the reference cantilever 3 and the deformable part 22 of the test cantilever 2 due to the interaction with the analyte 90.

The deformation of the deformable part 22 of the test cantilever 2 is shown for example for the test cantilever 2 in FIG. 2B. However, the description is analogous in respect of the reference cantilever 3. The reason for this is that the upper surface 260 and the upper surface 262 of the test cantilever 2 are extended to different degrees because of the interaction with the analyte 90, resulting in deformation of the test cantilever 2. Because of the great extent D at the upper surface 260, the first and second test transducers 200, 220 applied thereto can register an extension force F. The registered extension force F can be converted here to an electronic signal by the test transducers 200, 220 or influence an existing electronic signal, for example an applied voltage. This can be accomplished, for example, in that the test transducers 200, 220 change resistance if they experience an extension force F that in turn results in extension of the test transducers 200, 220.

As shown in FIG. 2B, the first and second test transducers 200, 220 may be arranged in a depression in the test cantilever 2. The depression increases the elasticity of the test cantilever 2, whereas the first and second test transducers 200, 220 increase the stiffness of the test cantilever 2. The combination of the two effects can achieve the effect that the first and second test transducers 200, 220 measure the extension of a test cantilever with high elasticity, which can generate a particularly large measurement signal with the test transducers 200, 220. If the test transducers 200, 220 were arranged solely on the surface of the cantilever 2, 3 and not in a depression, the test cantilever 2 would be stiffer, especially in the region of the respective transducers, and so a weaker measurement signal would be generated.

The depressions may have a depth of more than 5%, preferably more than 20%, more preferably more than 50%, of the thickness of the test cantilever 2. In the present case, in FIG. 2B, the depth is about 80% of the thickness of the cantilever 2, 3.

In addition, the height of the first and second test transducers 200, 220 corresponds to the depth of the respective depression, such that the upper surface of the test transducers 200, 220 concludes flush with the upper surface 260 of the test cantilever 2. It is also possible that the test transducers 200, 220 project beyond the upper surface 260, as shown in FIG. 2C, or lie partly beneath the upper surface 260, as shown in FIG. 2D, or lie entirely beneath the upper surface 260 (not shown).

Figure 2C:
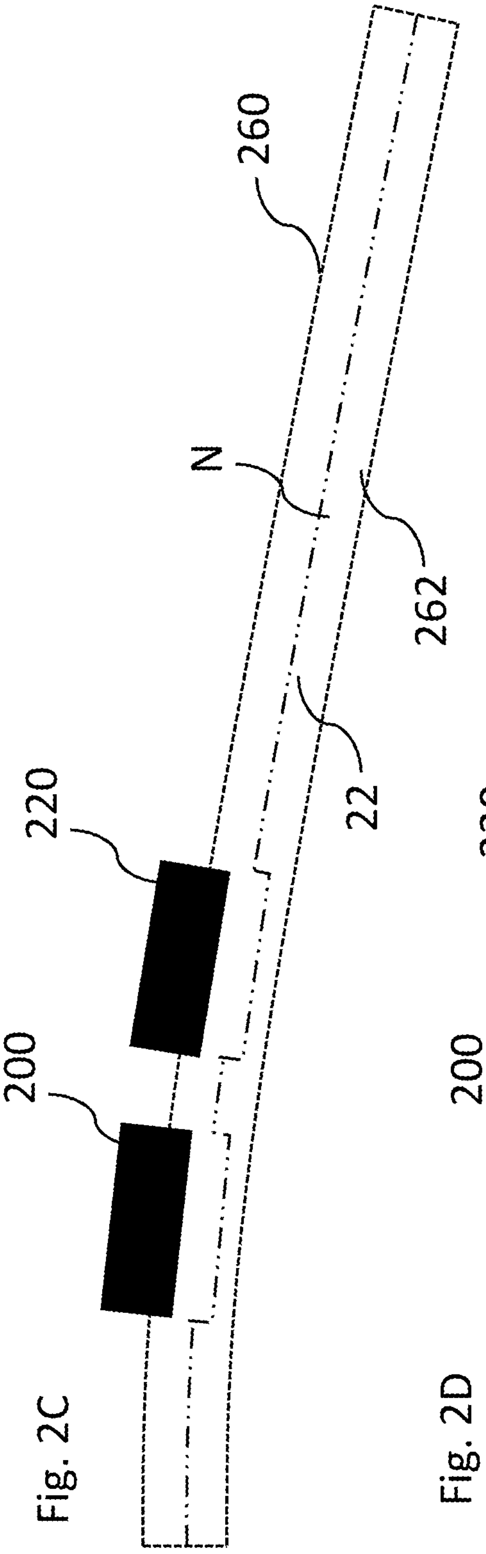
Figure 2D:
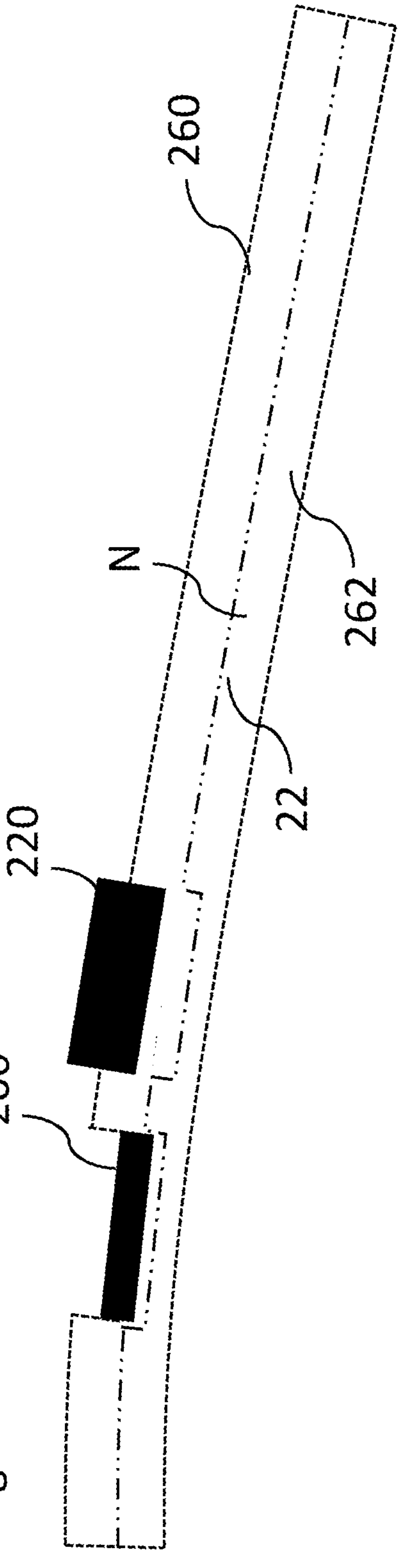
Figure 2E:
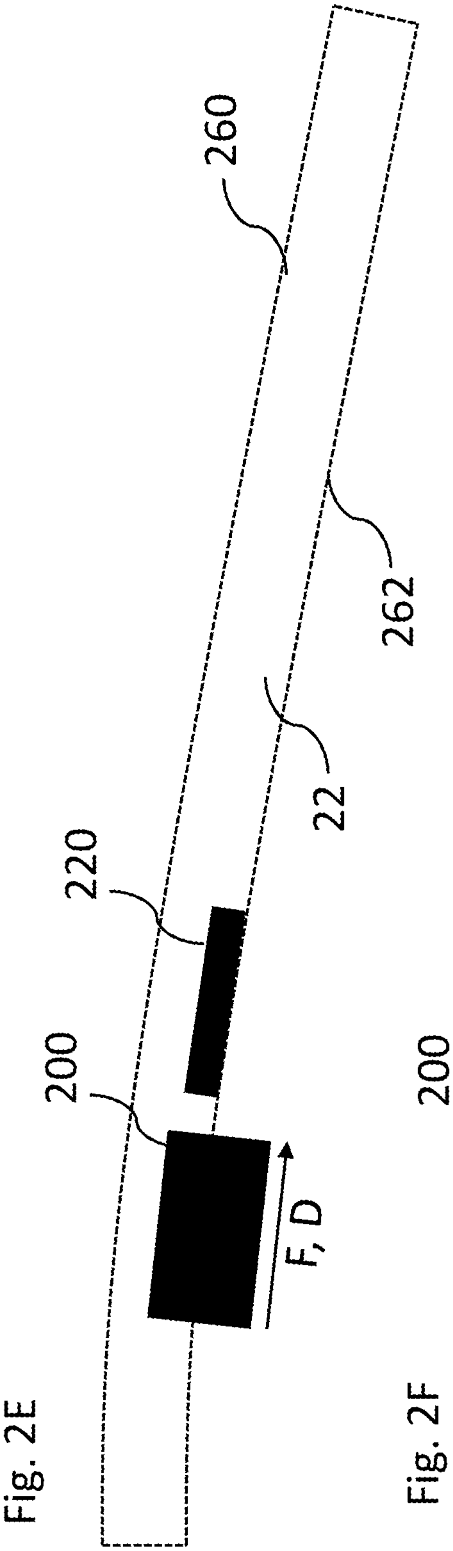

Moreover, the neutral axis N is drawn in in FIGS. 2C and 2D, along which no material stress occurs in the ground state, taking account in particular of the layer structure as well. The neutral axis N may be determined, for example, via computer simulations of the layer system having the geometry of the cantilever.

Figure 2F:
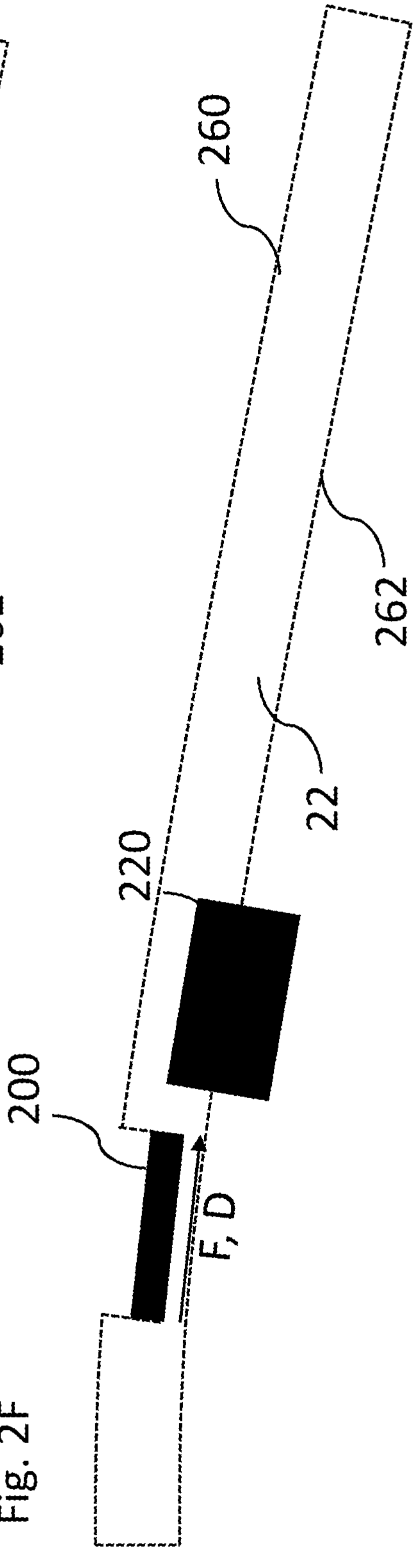

The first and second test transducers 200, 220 of the test cantilever 2 may also be arranged in depressions arranged on the lower surface of the test cantilever 2, as shown in 2E. In particular, it is also possible that the depression for the first test transducer 200 is arranged on the upper surface of the test cantilever 2, while the depression for the second test transducer is arranged on the lower surface (or vice versa), as shown in FIG. 2F. In particular, the test transducers 200, 220 may also have different thicknesses.

Beam theory makes it possible, for example, to predict the points on the deformable part 22 at which the extension D will be at its greatest. It is possible to arrange the test transducers 200, 220 at these points in order to achieve an optimal signal-to-noise ratio and in order to have maximum sensitivity to the extensions. In the exact positioning of the test transducers, however, other boundary conditions should also be taken into account. In particular, the test transducers 200, 220 may also be arranged at the sites on the test cantilever 2 with the greatest changes in extension on contact with a sample.

Figure 3A:
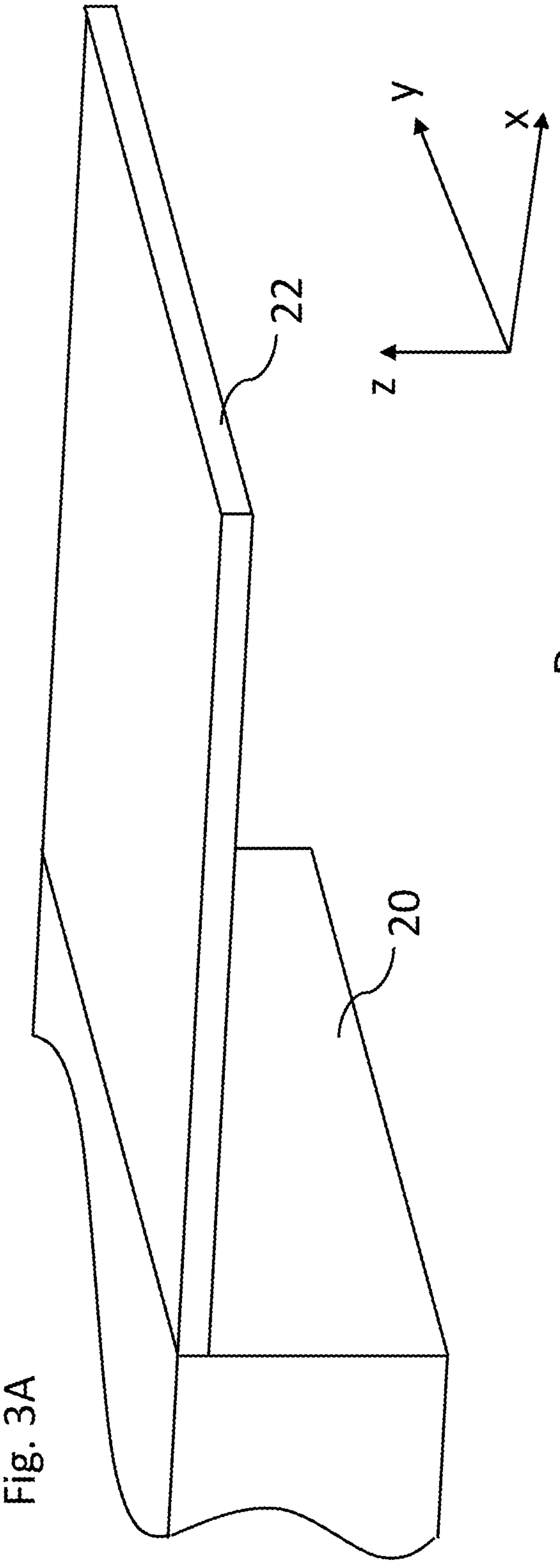
FIG. 3A-3D are schematic diagrams of the cantilever with longitudinal extents and transverse extents.
Figure 3B:
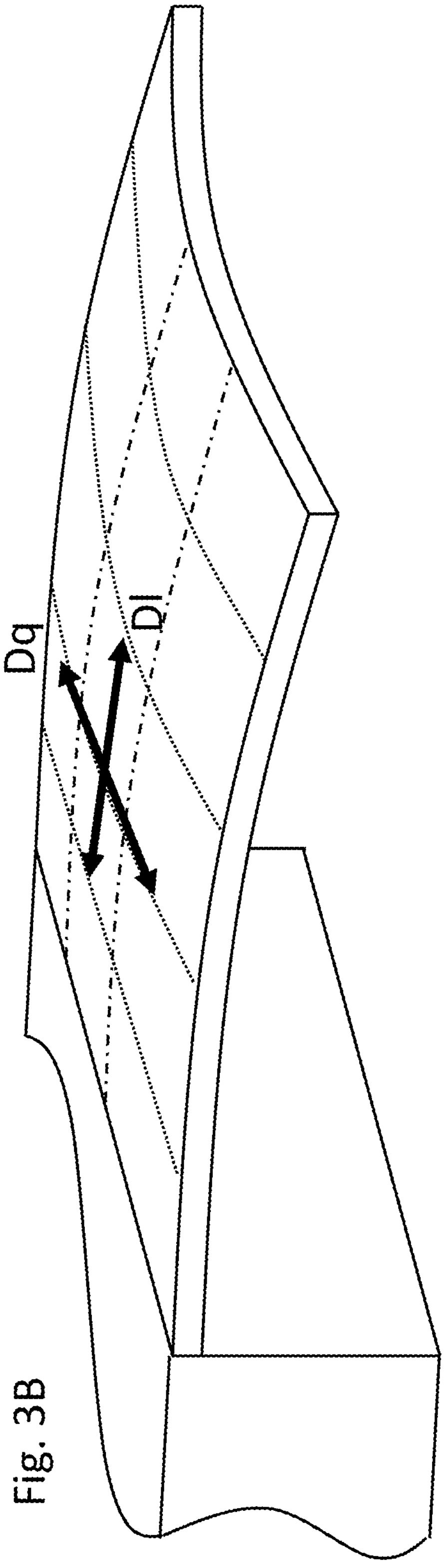

In particular, the alignment of the test transducers 200, 220 relative to the alignment of the cantilevers plays an important role. FIG. 3A shows, for example, a test cantilever in the ground state. If the test cantilever 2 comes into contact with the analyte 90, the surface tension changes and there is deformation of the material, as shown in FIG. 3B. FIG. 3B illustrates that the test cantilever undergoes deformation perpendicular to the base 20, or to the bending edge. This is accompanied by a longitudinal extension Dl of the upper surface. At the same time, deformation takes place parallel to the base 20, or to the bending edge, which is accompanied by a transverse extension Dq of the upper surface. The geometry of the test cantilever 2 makes it possible to determine the direction in which a greater extension D is brought about. In particular, the test transducers 200, 220 be aligned in these directions in order to generate a particularly large measured signal.

Figure 3C:
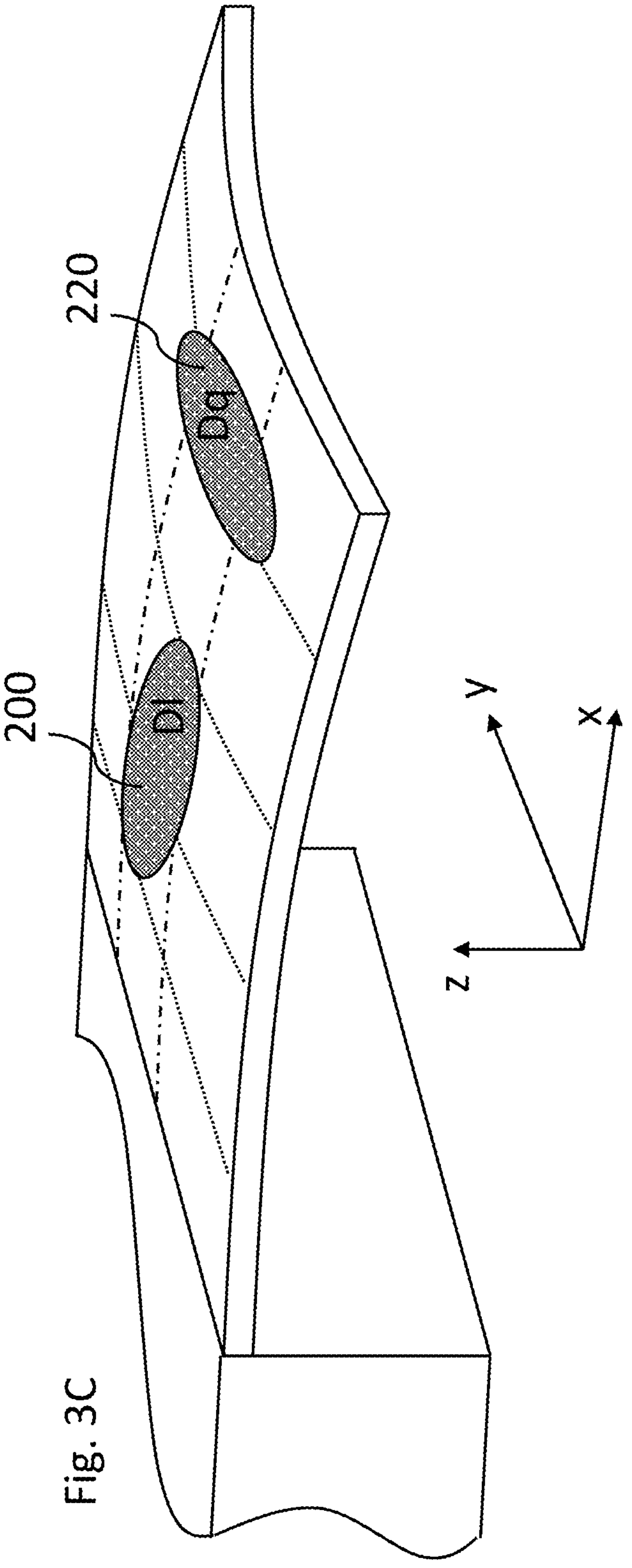

FIG. 3C shows for example that a first test transducer 200 is arranged at the site of the greatest longitudinal extent of the test cantilever 2, while a second test transducer 220 is arranged at the site of the greatest transverse extent of the test cantilever 2. The test transducers 200, 220 are in elliptical form here, but they may also have a rectangular profile, as shown in FIG. 2. In particular, the two test transducers 200, 220 are aligned differently with regard to the longitudinal axis of the test cantilever 2. The orientation of the test transducers 200, 220 may be guided, for example, by the long axis of the elliptical test transducer 200, 220. Accordingly, an isotropic transducer material, by virtue of the geometric configuration, can detect a longitudinal or transverse extension or else a mixed state.

The orientation of the transducers results from a preferential direction of the transducers in which these have the greatest possible sensitivity. This is typically at its highest in the direction of the greatest extent of the transducers. In the case of a configuration of the transducers with a rectangular base area, the preferential direction extends correspondingly along the longer side of the rectangle. In the case of the elliptical base area of the transducer indicated here, the preferential direction extends along the main axis.

The first test transducer 200 here is aligned parallel to the longitudinal axis of the test cantilever 2, while the second test transducer 220 is aligned perpendicular to the longitudinal axis of the test cantilever 2. In particular, the two test transducers 200, 220 are thus oriented perpendicular to one another and form an angle of 90°. However, the angle may also be smaller or greater, according to the nature and characteristics of the test cantilever and the test transducers 200, 220.

Figure 3D:
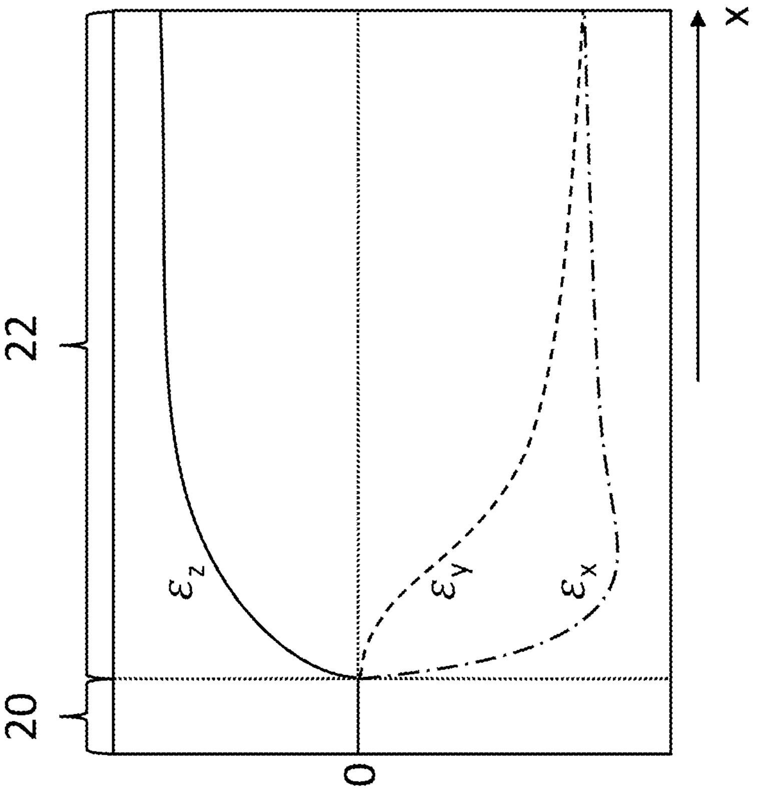

FIG. 3D shows a schematic of the progression of the extension of the test cantilever in FIG. 3C along the x axis. The extension here disappears along the base 20 and falls in terms of magnitude from the bending edge in the deformable part 22. In particular, the longitudinal extent along the x axis and the transverse extent along the y axis of different magnitudes.

The above description of FIGS. 2 and 3 is analogously applicable to the manner of function of the reference cantilever 3 with the first and second reference transducers 300, 320.

Figure 4A:
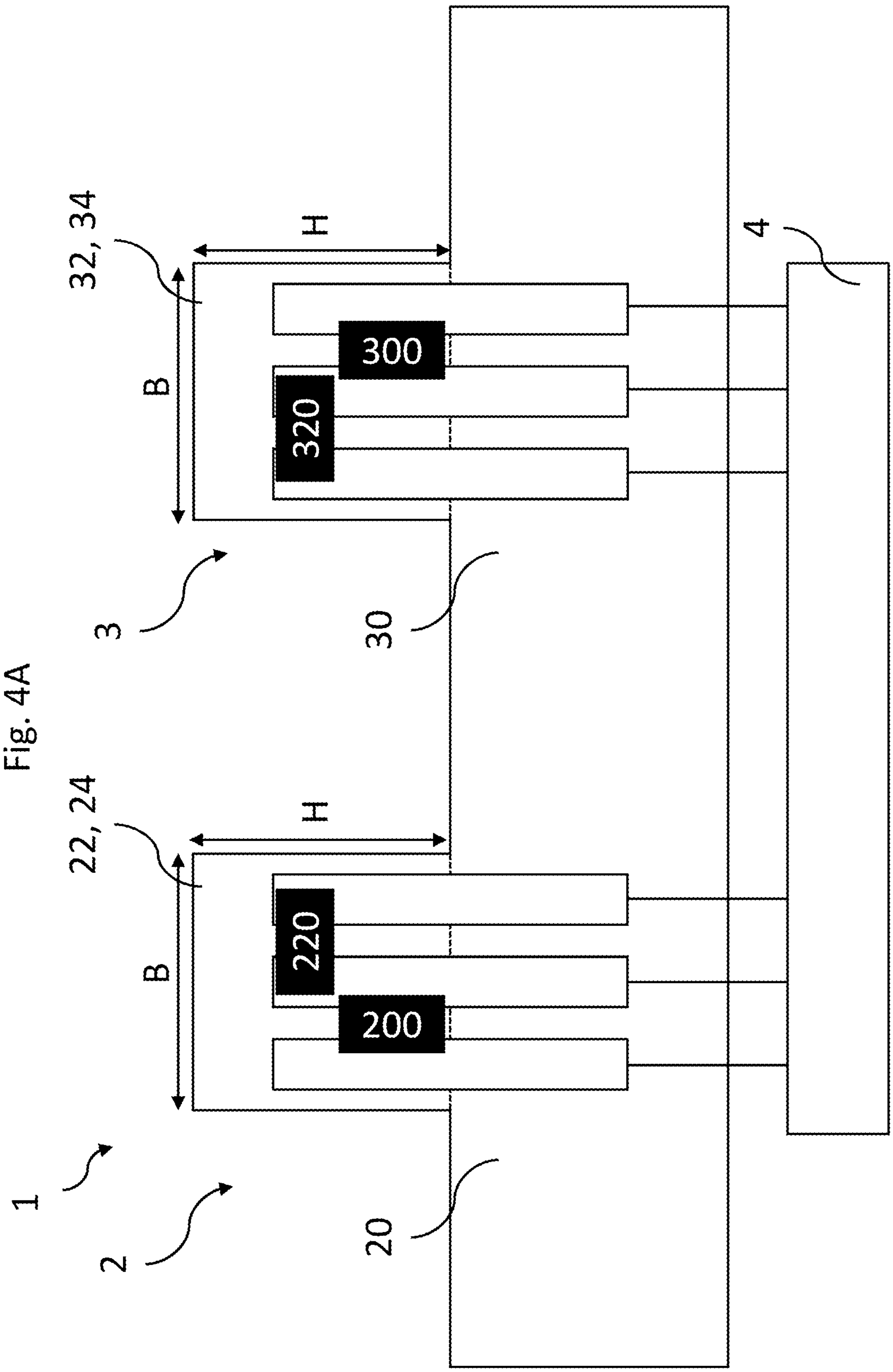
FIGS. 4A and 4B are additional schematic diagrams of the sensor and configurations of the transducers.

FIG. 4A shows an embodiment of the sensor 1 in which the reference cantilever 3 and the test cantilever 2 have identical geometric dimensions and have a mirror-symmetric configuration relative to one another. In particular, the height, width and thickness of the reference cantilever 3 correspond to the height, width and thickness of the test cantilever 2. This generates an equal extension D on the upper surfaces 260, 360. Because the geometrical dimensions of the cantilevers 2, 3 are identical, an identical dependence of the measured signal on the extension is accordingly also expected.

For example, the width B of the cantilevers is equal to the height H of the cantilevers 2, 3, which enables a particularly large extension D on the upper surface 260, 360 of the cantilever 2, 3. For example, the cantilevers here have a width of less than 150 μm, a length of less than 150 μm and a thickness of less than 1 μm, in particular a width of 50 μm, a length of 50 μm long and a thickness of 0.5 μm.

In the embodiment of the sensor 1 in FIG. 4A, the bases 30, 20 of the reference and test cantilevers 3, 2 are additionally arranged on the same overall base, which allows the cantilevers 2, 3 to be arranged closer to one another in order to reduce different environmental conditions.

Figure 4B:
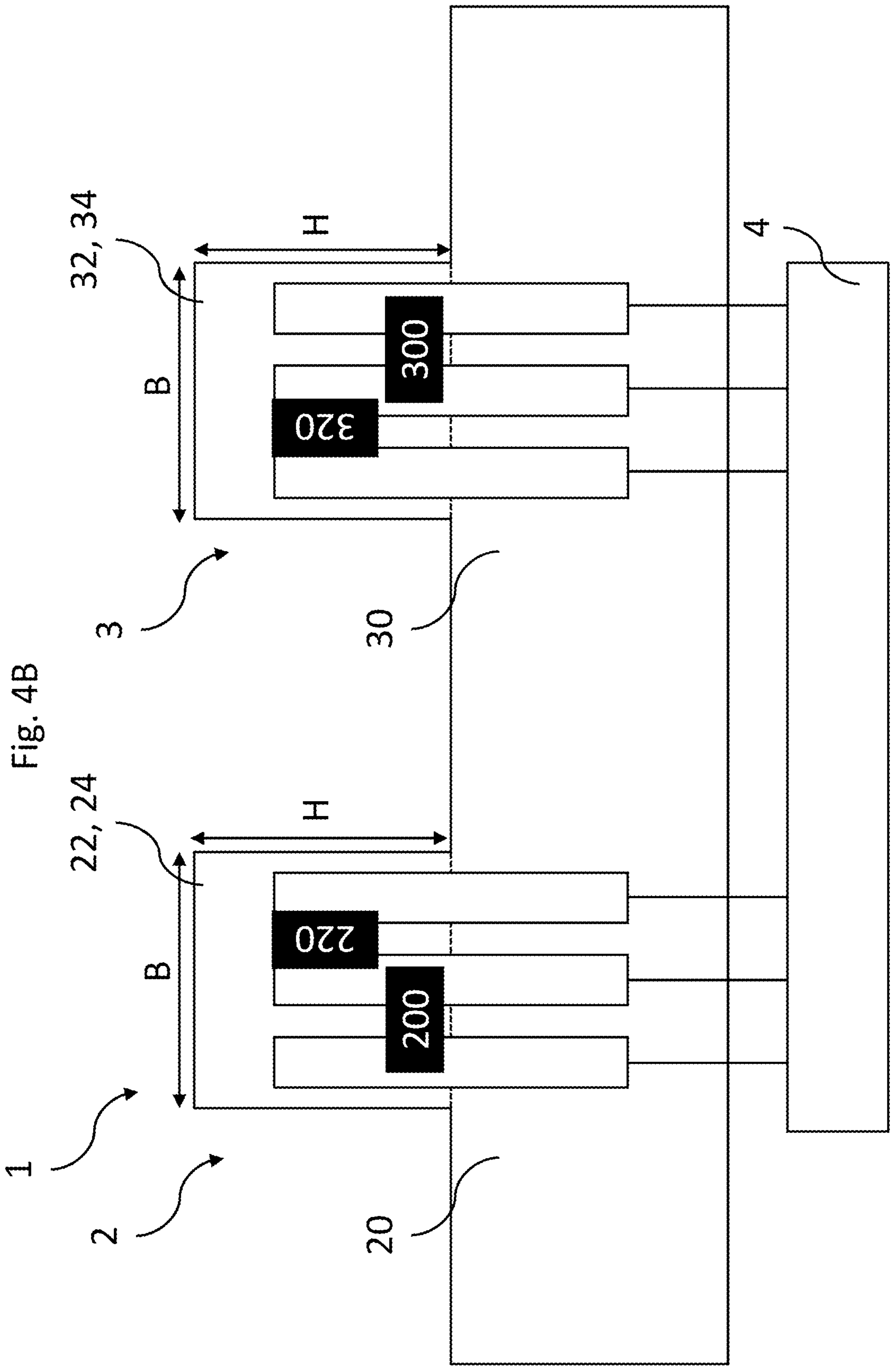

FIG. 4B shows a further embodiment in which the first transducers 200, 300 are aligned perpendicular to the longitudinal axis of the cantilever 2, 3, and the second transducers 220, 320 are aligned parallel to the longitudinal axis of the cantilever 2, 3. For comparison, FIG. 4A shows the first transducers 200, 300 aligned parallel to the longitudinal axis of the cantilevers 2, 3, while the second transducers are aligned perpendicular to the longitudinal axis of the cantilevers 2, 3.

Because the first transducers 200, 300 measure, for example, a transverse extent of the cantilevers 2, 3 and the second transducers 220, 320 measure a longitudinal extent, the difference in the measurement signals from the first transducers 200, 300 or the second transducers 220, 320 is attributable solely to the interaction or non-interaction of the analyte with the cantilevers.

In particular, the transducers 200, 220, 300, 320 shown may be arranged and aligned not only on the surface of the cantilevers 2, 3, but may also be arranged in a corresponding depression.

Figure 5A:
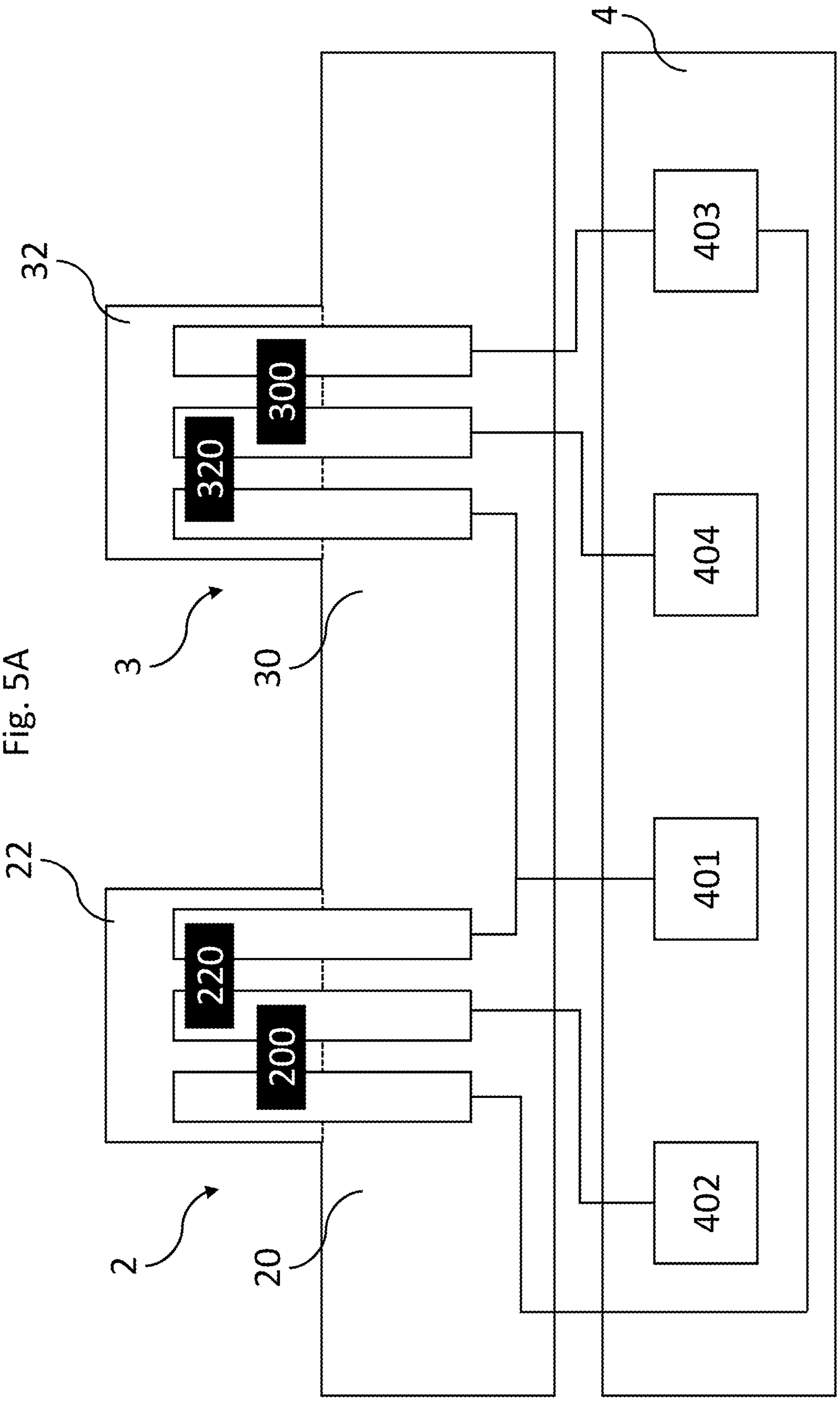
FIGS. 5A and 5B are additional schematic diagram of the sensor together with sensor electrodes.

FIG. 5A shows a further embodiment of the sensor 1. The transducers 200, 220, 300, 320 are in electrically connected via the electrodes 401, 402, 403, 404. In particular, the second test transducer 220 is connected to the second reference transducer 320 via the electrode 401. In addition, the first test transducer 200 is connected to the first reference transducer 300 via the electrode 403. The second test transducer 220 is additionally connected to the first test transducer 200 via the electrode 402, while the second reference transducer 320 is connected to the first reference transducer 300 via the electrode 404. The result is thus a total of four electrodes 200, 220, 300, 320 via which the transducers are electrically contact-connected to one another.

Figure 5B:
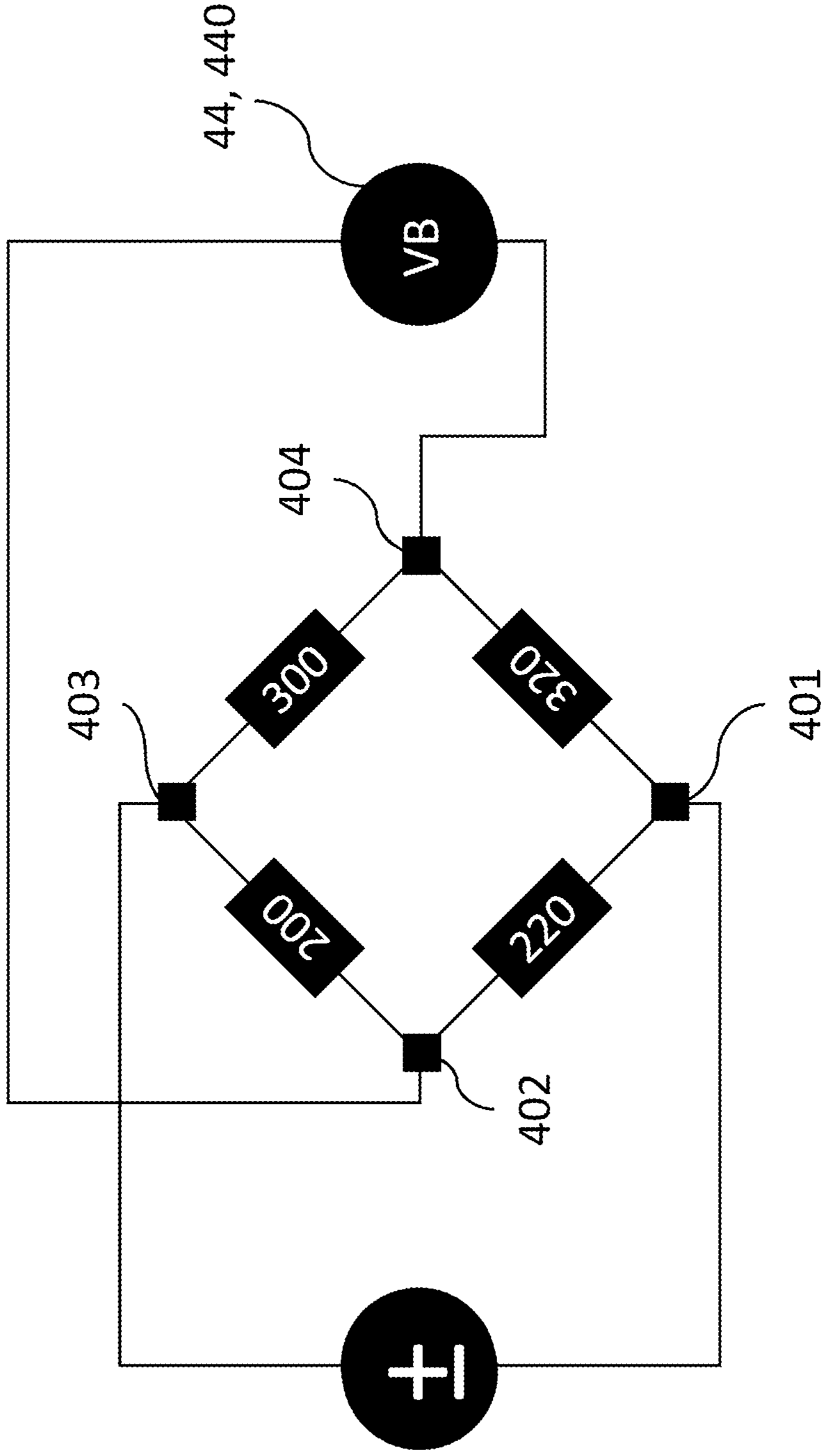

The transducers 200, 220, 300, 320 are in particular electrically interconnected in what is called a full bridge. The circuit of the full bridge is shown in FIG. 5B. In the full bridge, a DC voltage or AC voltage is applied between the electrodes 403, 401. The first and second transducers act as a voltage divider between these electrodes due to their electrical resistances. A full bridge in the form shown has the advantage that no voltage is established between the electrodes 402, 404 if the ratio of the resistances of the first test transducer 200 to the second test transducer 220 of the test cantilever 2 is equal to the ratio of the resistances of the first reference transducer 300 to the second reference transducer 320 of the reference cantilever 3. Even the variance of one resistance is thus sufficient in order to change the resistance ratios, and thus in order to establish a voltage between the electrodes 402, 404.

When the reference cantilever 3 and the test cantilever 2 interact with the sample 9 and the analyte 90, both deformable parts 22, 32, for example, experience a change in surface tension, which is greater for the deformable part 22 of the test cantilever 2 than for the deformable part 32 of the reference cantilever 3.

Because the resistances of the first and second transducers change differently because of the different alignment, for example, a particularly large change in resistance ratios results from the deformation of the deformable part 22 of the test cantilever 2 due to the interaction with the analyte 90 in the sample 9, which interacts specifically with the reference layer 24 of the test cantilever 2. In the event of such an interaction, a voltage is accordingly established between the electrodes 402, 404, such that a force exerted on the first and second test transducers 200, 220 relative to the first and second reference transducers 300, 320 can be displayed in the form of a cross-bridge voltage VB. The cross-bridge voltage VB is preferably proportional to the occurrence of the analyte 90 in the sample 9, thereby enabling a quantitative assessment of the measured signal.

A cross-bridge voltage detector 44 can display the cross-bridge voltage VB externally or forward it, such that the existence of a cross-bridge voltage VB is made visible to the user of the sensor 1. In particular, such a cross-bridge voltage detector 44 may also be formed by an A/D converter, where the A/D converter converts the cross-bridge voltage VB to a digital signal that can be forwarded to an external measuring device. It may also be the case that the detector 44 detects the signals at the electrodes 402 and 404 in isolation from one another, such that it is possible to draw a conclusion as to the respective deflections of the deformable parts 32, 22.

Figure 6:
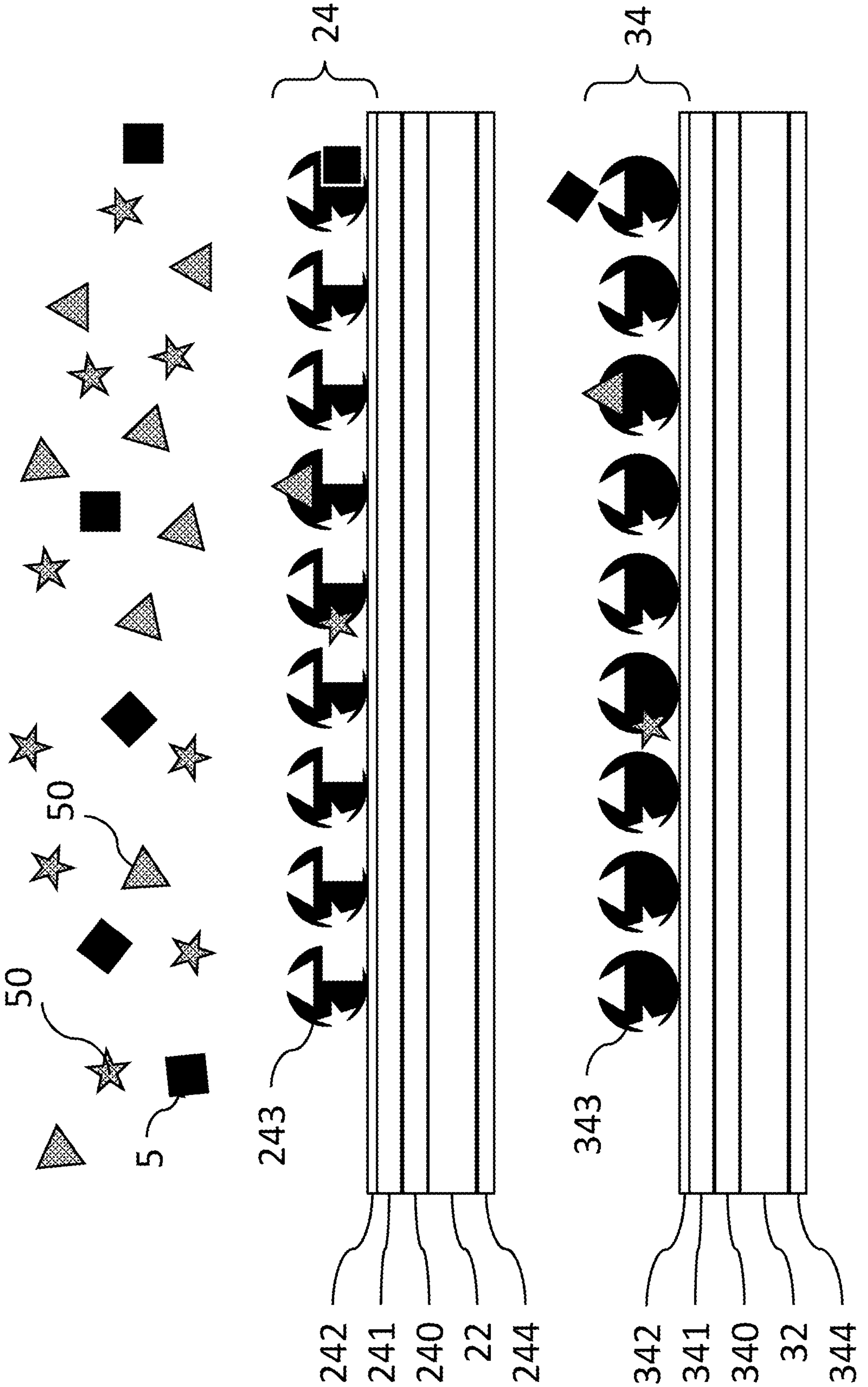
FIG. 6 is a schematic diagram of the binding of antigens to antibodies.

FIG. 6 shows a schematic of the structure of the various deformable parts 22, 32 of the reference and test cantilevers 3, 2. The construction of the cantilevers is identical apart from the receptor layer and the reference layer, meaning that an interaction with the sample or the surrounding medium, along with the mechanical configuration of the cantilever, is very substantially identical.

An activation layer 34, 24 is applied to the deformable part 32, 22 of the reference and test cantilever 3, 2, respectively. An activation layer 240 is configured to promote adhesion between the surface of the deformable part 32, 22 and a further layer 241, 341. A task of the activation layer 240 is furthermore to bring about an asymmetric layer structure of the cantilever 3, 2, such that there is the greatest possible difference in the extent of the upper surface of the cantilever and the lower surface of the cantilever.

A so-called self-assembly monolayer 241 may then be applied to the gold layer 240, and this can compensate for the surface unevenness of the gold layer and at the same time provides adhesion promotion for a further layer, specifically the reference and receptor layers 34, 24.

The structure of the reference and receptor layer 34, 24 is different. However, both layers are based on a layer that may comprise a so-called protein A 242, which firstly binds to the self-assembly monolayer 241, 341, but also has and is able to bind, on its surface, antibodies 243 or isotype control antibodies 343.

The antibodies 243 are proteins that react or bind to an antigen 5 and hence, for example, mark virus cells in the human immune system, such that the immune system is accordingly able to destroy the marked virus in order, for example, to stem or to prevent a viral outbreak. The antibodies 243 are very substantially specific to the antigen 5, but may also interact with other similar antigens 50. FIG. 6 shows that the antibody 243 can interact with the antigen 5 and the similar antigens 50 to some degree.

In contrast to the antibody 243, the isotype control antibody 343 is a protein that preferentially does not interact with the antigen 5 with ultrahigh specificity. This makes it possible to virtually rule out any interaction with a specific antigen 5. This is shown in FIG. 6 in that the isotype control antibody 343 can interact only with two similar antigens 50, but not with the antigen 5 which is shown schematically as a square here. As a result, the relative change in surface tension of the cantilevers 22, 32 is attributable solely to the specific antigen 5.

Because the test cantilever 2 has an antibody 243 and the reference cantilever 3 has an isotype control antibody 343, it is ensured that, in the sample 9, the analyte 90, if the analyte 90 is an antigen 5, is able to interact solely with the test cantilever 2. This ensures that the relative deformation brought about by the analyte 90 in the test cantilever 2, in comparison with the deformation of the reference cantilever 3, is based solely on the presence of the analyte 90 or of the antigen 5. Accordingly, it is possible with this sensor 1 to reliably and quickly detect an antigen 5.

In contrast to the upper surface of the cantilevers 2, 3, the lower surface of the cantilevers is passivated. Such a passivation 244 and 344 may have the effect that an interaction, or binding, or absorption or adsorption, of an analyte 90 in the sample 9 in or on the cantilevers is avoided. However, such a passivation layer in particular also contributes to an increase in the asymmetry of the layer structure in order to bring about the greatest possible extension effect on the upper surface of the cantilever 3, 2. In particular, the passivation layer may comprise trimethoxysilane and/or a blocking substance.

Where applicable, all individual features that are illustrated in the embodiments may be combined with one another and/or exchanged for one another without departing from the scope of the invention.

LIST OF REFERENCE SIGNS

1 sensor
10 bending edge
2 test cantilever
20 base
200 first test transducer
22 deformable part
220 second test transducer
24 receptor layer
240 activation layer
241 self-assembly monolayer
242 protein A
243 antibody
244 passivation layer
26 surface
260 upper surface
262 lower surface
3 reference cantilever
30 base
300 first reference transducer
32 deformable part
320 second reference transducer
34 reference layer
340 activation layer
341 self-assembly monolayer
342 protein A
343 isotype control antibody
344 passivation layer
36 surface
360 upper surface
362 lower surface
4 electronics
40 electrode
400, 401, 402, 403 electrodes
42 cross-bridge voltage detector
44 A/D converter
440 A/D converter logic unit
5 antigen
50 similar antigen
9 sample
90 analyte
F force
L deflection
D extension
AT distance between active and passive transducer
AE distance between electrodes
S axis of symmetry
VB cross-bridge voltage
N neutral axis

The invention claimed is:

1. A sensor for converting into an electrical signal at least one of chemical and biochemical information of an analyte in a sample, the sensor comprising:

a test cantilever; and a reference cantilever; wherein the test cantilever comprises a test cantilever base, a first test cantilever test transducer atop the test cantilever, a second test cantilever test transducer atop the test cantilever, and a test cantilever deformable part having a receptor layer configured to selectively uptake at a first affinity the analyte applied atop the test cantilever deformable part;

the reference cantilever comprises a reference cantilever base, a first reference cantilever test transducer atop the reference cantilever, a second reference cantilever test transducer atop the reference cantilever and a reference cantilever deformable part having a reference layer configured to selectively uptake the analyte applied atop the deformable part at a second affinity lower than the first affinity; and the first test cantilever test transducer, the second test cantilever test transducer, the first reference cantilever test transducer and the second reference cantilever test transducer are configured to output an electrical signal corresponding to at least one of a detection of the analyte in the sample, the concentration of the analyte in the sample and the amount of the analyte in the sample.

2. The sensor according to claim 1, wherein the first test cantilever test transducer and the second test cantilever test transducer are configured to ascertain a test cantilever surface tension change; and the first reference cantilever test transducer and the second reference cantilever test transducer are configured to ascertain a reference cantilever surface tension change.

3. The sensor according to claim 1, wherein the first test cantilever test transducer, the second test cantilever test transducer, the first reference cantilever test transducer and the second reference cantilever test transducer are each configured to detect at least one of a bending force, an extension force, a shear force, and a surface tension.

4. The sensor according to claim 1, wherein the test cantilever deformable part has a first dimension and the reference cantilever deformable part has a second dimension identical to the first dimension.

5. The sensor according to claim 1, wherein the reference cantilever comprises at least one of Si and aluminium oxide; and the test cantilever comprises at least one of Si and aluminium oxide.

6. The sensor according to claim 1, wherein the first test cantilever test transducer has a first intrinsic physical property;

the second test cantilever test transducer has a second intrinsic physical property;

the first reference cantilever test transducer has a third intrinsic physical property;

the second reference cantilever test transducer has a fourth intrinsic physical property; and the first intrinsic physical property, the second intrinsic physical property, the third intrinsic physical property and the fourth intrinsic physical property are identical.

7. The sensor according to claim 1, further comprising a first electrode, a second electrode, a third electrode and a fourth electrode wherein the first electrode is configured to electrically contact the first test cantilever test transducer;

the second electrode is configured to electrically contact the second test cantilever test transducer;

the third electrode is configured to electrically contact the first reference cantilever test transducer;

the fourth electrode is configured to electrically contact the second reference cantilever test transducer;

the first test cantilever test transducer has a first electrical property;

the second test cantilever test transducer has a second electrical property;

the first reference test cantilever transducer has a third electrical property;

the second reference test cantilever transducer has a fourth electrical property; and the first test cantilever test transducer, the second test cantilever test transducer, the first reference cantilever test transducer and the second reference cantilever test transducer are electrically connected in a full bridge configured to establish a cross-bridge voltage based the first electrical property, the second electrical property, the third electrical property and the fourth electrical property.

8. The sensor according to claim 7, wherein the full bridge includes a cross bridge voltage and the sensor further comprises a cross-bridge voltage detector configured to detect the cross-bridge voltage (VB) of the full bridge.

9. The sensor according to claim 1, wherein the test cantilever comprises a common test cantilever depression or a first test cantilever depression and a second test cantilever depression;

the first test cantilever test transducer is arranged in the first test cantilever depression and the second test cantilever test transducer is arranged in the second test cantilever depression or the first test cantilever test transducer and the second test cantilever test transducer are arranged in the common test cantilever depression; and the reference cantilever comprises a common reference cantilever depression or a first reference cantilever depression and a second reference cantilever depression; and the first reference cantilever test transducer is arranged in the first reference cantilever depression and the second reference cantilever test transducer is arranged in the second reference cantilever depression or the first reference cantilever test transducer and the second reference cantilever test transducer are arranged in the common reference cantilever depression.

10. The sensor according to claim 9, wherein the common test cantilever depression or the first test cantilever depression and the second test cantilever depression provide the test cantilever with a first elasticity; or the first test cantilever depression and the second test cantilever depression and the common reference cantilever depression or the first reference cantilever depression and the second reference cantilever depression provide the reference cantilever with a second elasticity.

11. The sensor according to claim 9, wherein the test cantilever has a test cantilever upper surface and a test cantilever lower surface;

the reference cantilever has a reference cantilever upper surface and a reference cantilever lower surface;

the common test cantilever depression or the first test cantilever depression and the second test cantilever depression are arranged on the test cantilever upper surface or on the test cantilever lower surface; and the common reference cantilever depression or the first reference cantilever depression and the second reference cantilever depression are arranged on the reference cantilever upper surface or on the reference cantilever lower surface.

12. The sensor according to claim 1, wherein the first test cantilever test transducer, the second test cantilever transducer, the first reference cantilever test transducer and the second reference cantilever test transducer are each configured to detect a longitudinal force component and a transverse force component.

13. The sensor according to claim 12, wherein the first test cantilever test transducer is orthogonal to the second test cantilever test transducer and the first reference cantilever test transducer is orthogonal to the second reference cantilever test transducer.

14. The sensor according to claim 12, wherein the test cantilever has a test cantilever maximum surface tension site and a test cantilever minimum surface tension site;

the reference cantilever has a reference cantilever maximum surface tension site and a reference cantilever minimum surface tension site;

the first test cantilever test transducer is arranged at the test cantilever maximum surface tension site;

the second test cantilever test transducer is arranged at the test cantilever minimum surface tension site;

the first reference cantilever test transducer is arranged at the reference cantilever maximum surface tension site; and the second reference cantilever test transducer is arranged at the reference cantilever minimum surface tension site.

15. The sensor according to claim 1, wherein the test cantilever has a test cantilever upper surface and a test cantilever lower surface;

the reference cantilever has a reference cantilever upper surface and a reference cantilever lower surface; and the test cantilever upper surface, the test cantilever lower surface, the reference cantilever upper surface and the reference cantilever lower surface define an activation layer comprising gold and providing an activation layer surface tension.

16. The sensor according to claim 1, wherein the test cantilever has a test cantilever upper surface and a test cantilever lower surface;

the reference cantilever has a reference cantilever upper surface and a reference cantilever lower surface;

the test cantilever upper surface, the test cantilever lower surface, the reference cantilever upper surface and the reference cantilever lower surface are a passivation layer comprising at least one of trimethoxysilane and a blocking substance and is configured to curtail non-specific protein adhesion.

17. The sensor according to claim 1, wherein the reference cantilever further comprises a first layer and the test cantilever further comprises a second layer.

18. The sensor according to claim 1, wherein the receptor layer comprises a receptor layer antibody against an antigen, and the reference layer comprises an antigen-specific isotype control antibody.

19. The sensor according to claim 1, wherein:

the receptor layer provides molecule-specific binding forces, and the reference layer does not provide molecule-specific binding forces;

the receptor layer comprises a first single-strand deoxyribonucleic acid (ssDNA) fragment, or a first DNA fragment binding specifically to a third DNA fragment in the sample, and the reference layer comprises a fourth single-strand DNA or a fifth DNA not binding to chemical, biochemical and physical species in the sample;

the receptor layer comprises a first single-strand ribonucleic acid RNA fragment a first RNA fragment binding specifically to a second RNA fragment in the sample and the reference layer comprises a third single-strand RNA or a fourth RNA fragment not binding to chemical, biochemical and physical species in the sample;

the receptor layer comprises a receptor layer antibody or a receptor layer protein, wherein the receptor layer antibody and the receptor layer protein is configured to specifically bind a target protein and the reference layer comprises a specific isotype control antibody or a protein, the specific isotype control antibody and the protein not binding to all chemical and biochemical and physical species in the sample;

the receptor layer comprises a single-chain variable fragment scFv antibody and the reference layer comprises a single-chain variable fragment scFv antibody-specific isotype control antibody;

the receptor layer comprises a Sars-COV2 antibody and the reference layer comprises a severe acute respiratory syndrome coronavirus 2 Sars-CoV2-specific isotype control antibody; or the receptor layer comprises a first hydrogel and the reference layer comprises a second hydrogel.

* * * * *